(12) United States Patent
John

(10) Patent No.: US 10,322,294 B2
(45) Date of Patent: Jun. 18, 2019

(54) SYSTEMS AND METHODS FOR VECTOR STIMULATION IN MEDICAL TREATMENT

(71) Applicant: Michael Sasha John, Larchmont, NY (US)

(72) Inventor: Michael Sasha John, Larchmont, NY (US)

( * ) Notice: Subject to any disclaimer, the term of this patent is extended or adjusted under 35 U.S.C. 154(b) by 472 days.

(21) Appl. No.: 14/474,289

(22) Filed: Sep. 1, 2014

(65) Prior Publication Data

US 2014/0371515 A1 Dec. 18, 2014

Related U.S. Application Data

(63) Continuation of application No. 11/626,372, filed on Jan. 23, 2007, now Pat. No. 8,825,166, which is a continuation of application No. 11/307,050, filed on Jan. 20, 2006, now Pat. No. 8,788,044.

(60) Provisional application No. 60/594,321, filed on Mar. 29, 2005, provisional application No. 60/596,693, filed on Oct. 13, 2005, provisional application No. 60/593,521, filed on Jan. 21, 2005, provisional application No. 60/766,499, filed on Jan. 23, 2006.

(51) Int. Cl.
*A61N 1/05* (2006.01)
*A61N 2/00* (2006.01)
*A61N 1/36* (2006.01)
*A61N 2/02* (2006.01)

(52) U.S. Cl.
CPC ........... *A61N 2/006* (2013.01); *A61N 1/3605* (2013.01); *A61N 2/02* (2013.01); *A61N 1/0529* (2013.01); *A61N 1/0531* (2013.01); *A61N 1/0534* (2013.01); *A61N 1/36021* (2013.01); *A61N 1/36025* (2013.01); *A61N 1/36071* (2013.01); *A61N 1/36082* (2013.01)

(58) Field of Classification Search
CPC .. A61N 1/0529; A61N 1/0531; A61N 1/0534; A61N 1/36021; A61N 1/36025; A61N 1/3605; A61N 1/36071; A61N 1/36082; A61N 2/006; A61N 2/02
See application file for complete search history.

(56) References Cited

U.S. PATENT DOCUMENTS

| | | | |
|---|---|---|---|
| 6,447,440 B1 * | 9/2002 | Markoll | A61N 2/02 128/898 |
| 7,520,848 B2 * | 4/2009 | Schneider | A61B 5/04009 600/13 |
| 2005/0182287 A1 * | 8/2005 | Becker | A61N 2/008 600/13 |

* cited by examiner

*Primary Examiner* — Amanda K Hulbert
(74) *Attorney, Agent, or Firm* — Rosenberg, Klein & Lee

(57) ABSTRACT

Stimulation treatments for medical disorders comprise providing stimulation parameters that create partial stimulation signals which combine into vector signals. The individual partial signals may have frequency or temporal content that is unique rather than all being identical. Vector signals may thus be designed with certain advantageous characteristics such as to influence target tissue in an intended manner while partial signals may be designed with other advantageous characteristics such as to avoid producing side effects in adjacent tissue. Roving of stimulation parameters can be designed to influence partial signals, vectors signals, or both. Partial and vector signals may be designed to match or avoid internal/endogenous activity patterns and rhythms of a patient. Methods for choosing, creating and using partial signals are disclosed. Tissue modulation may be accomplished with electrical and/or magnetic stimulation.

20 Claims, 10 Drawing Sheets

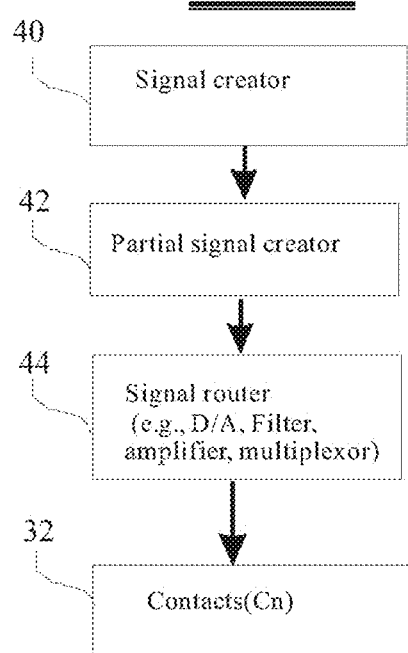
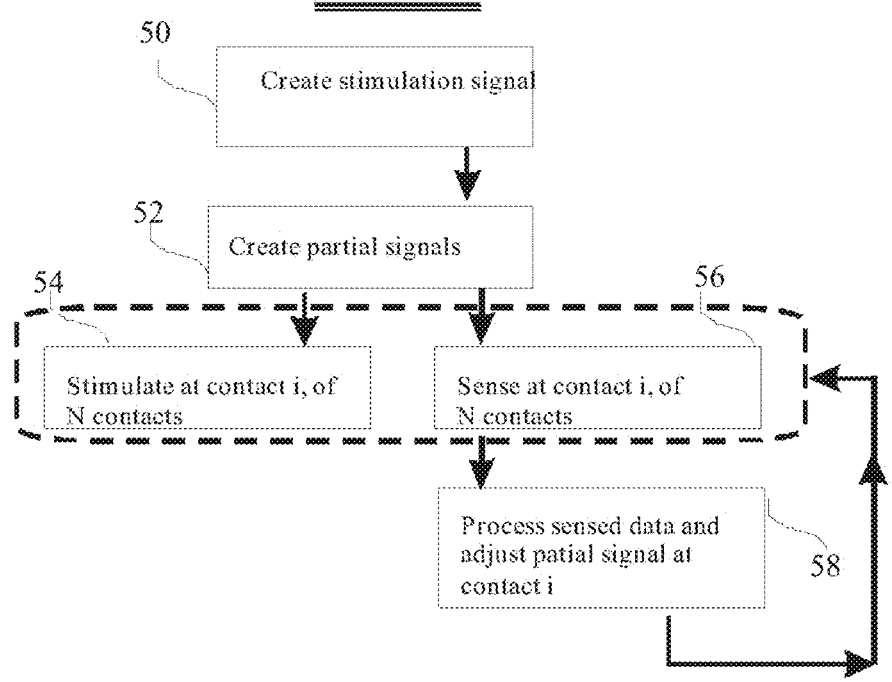

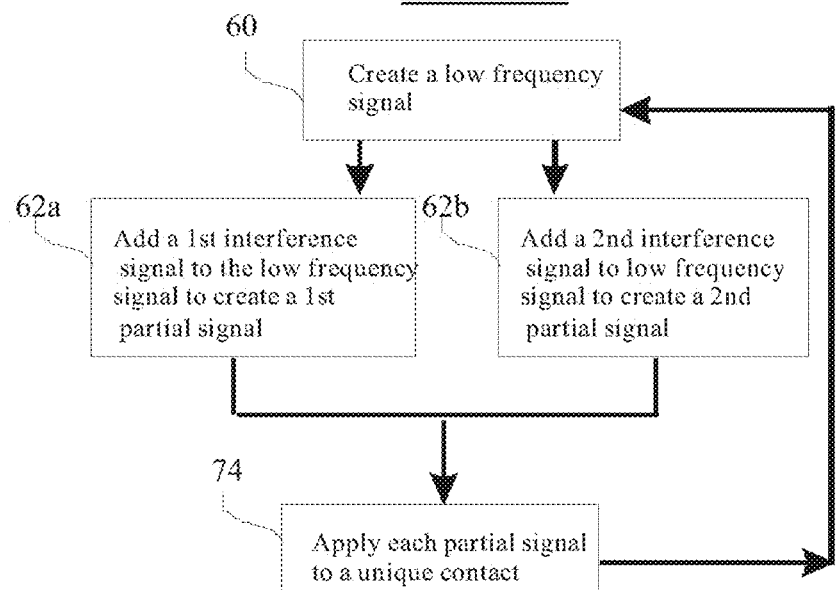
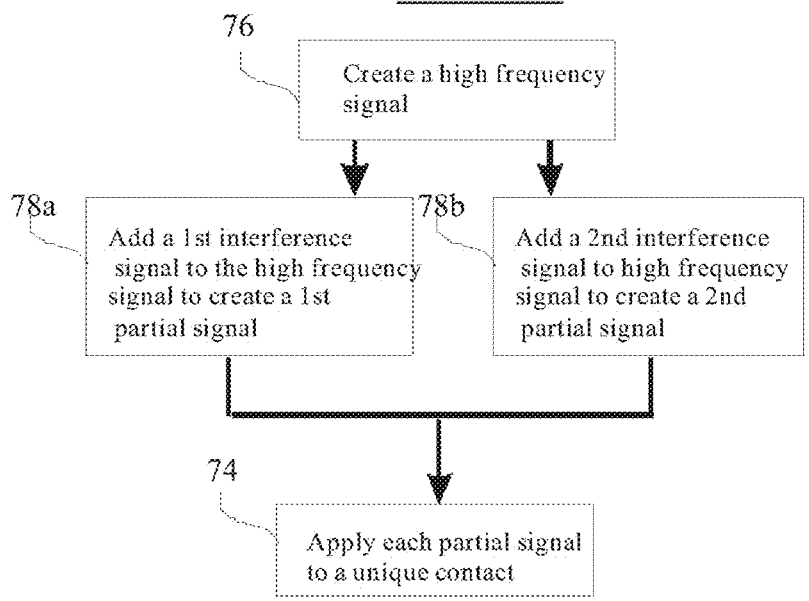

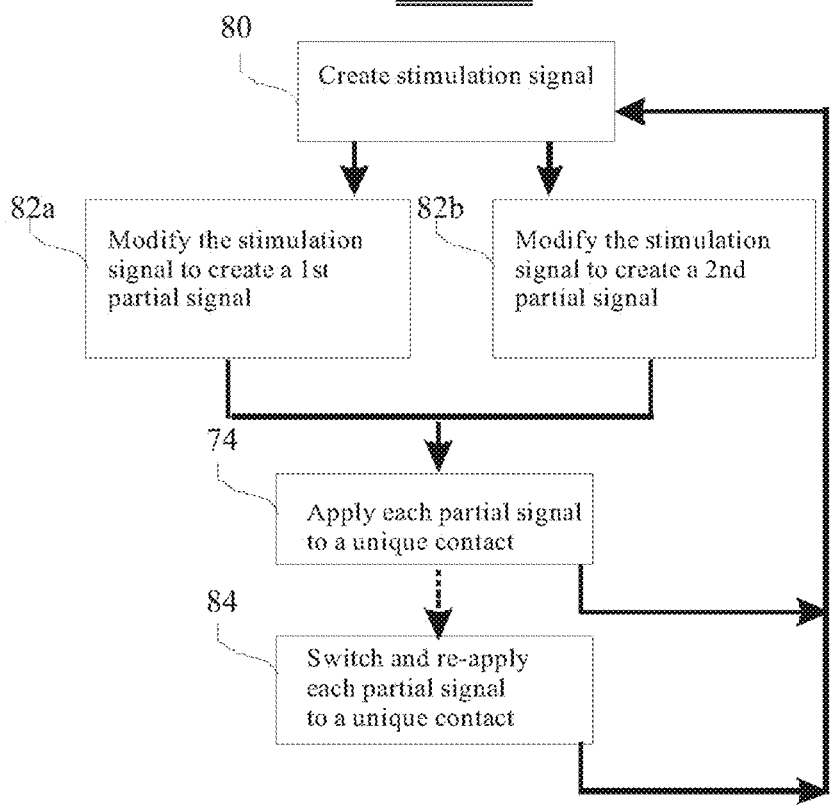
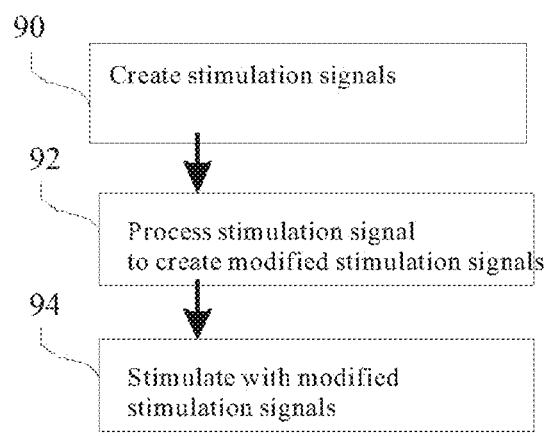

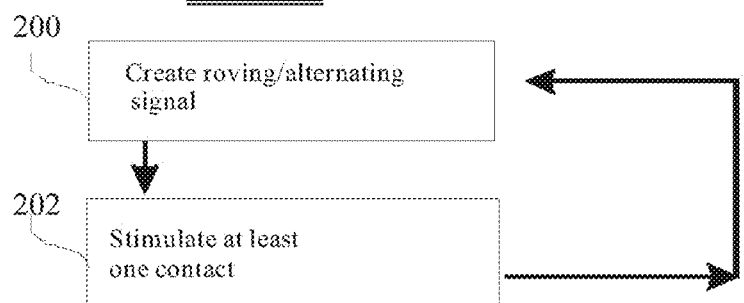
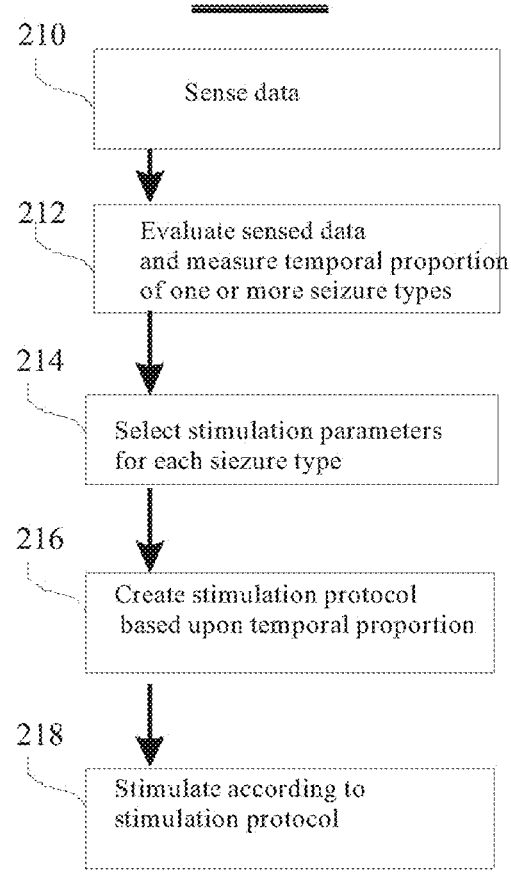

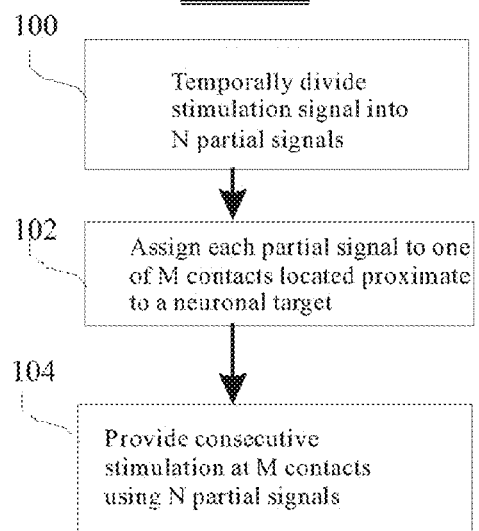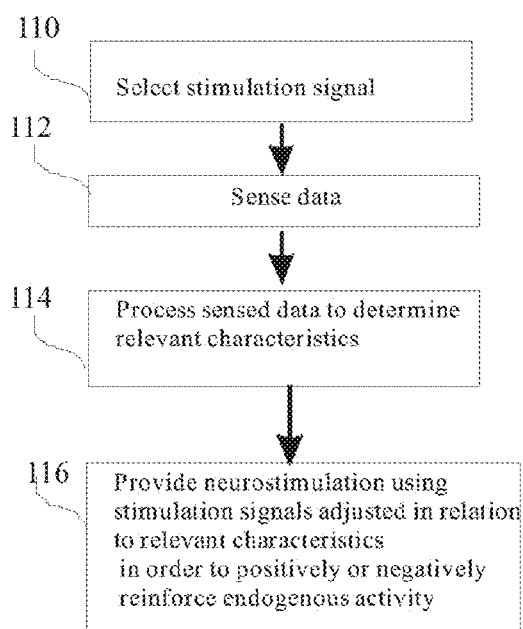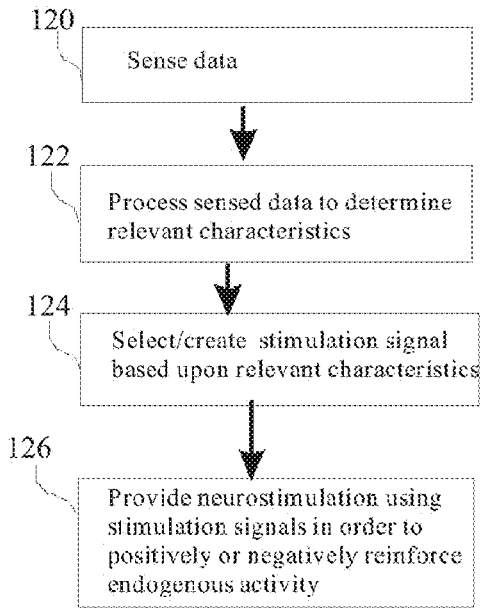

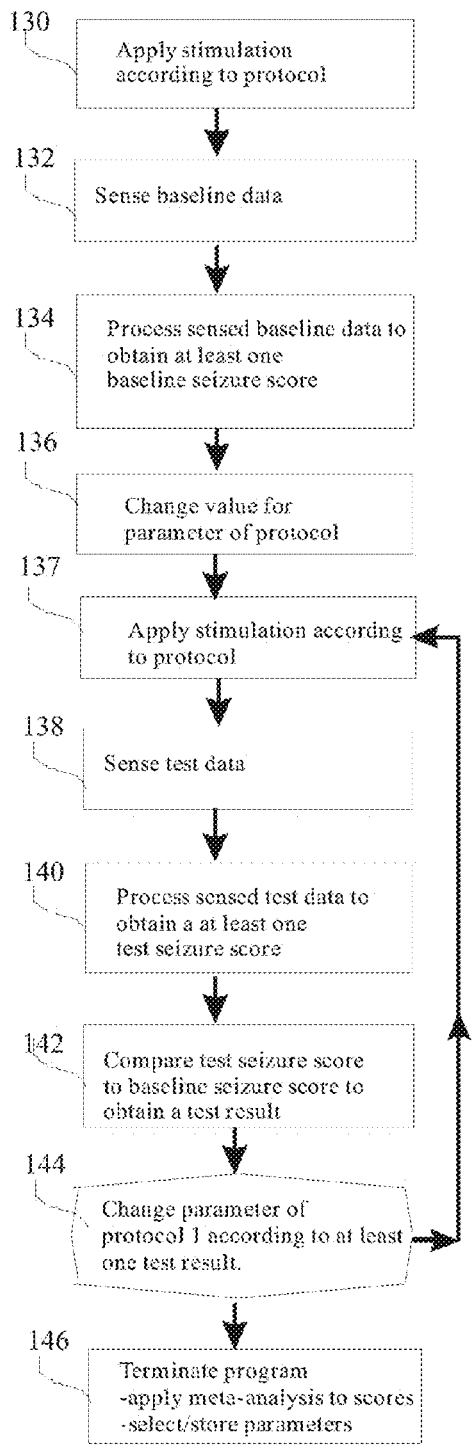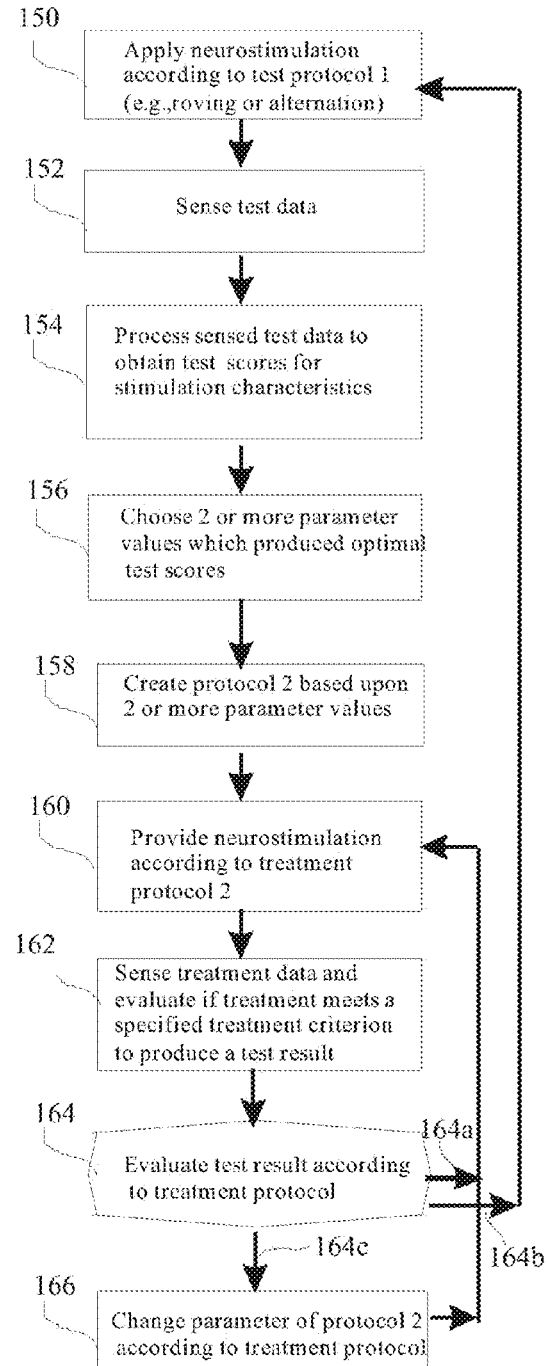

SYSTEMS AND METHODS FOR VECTOR STIMULATION IN MEDICAL TREATMENT

This application is a continuation of application Ser. No. 11/626,372, which is a continuation-in-part of application Ser. No. 11/307,050 filed Jan. 20, 2006, said application claiming priority of U.S. Provisional Application Nos. 60/594,321 filed on Mar. 29, 2005 and 60/596,693 filed on Oct. 13, 2005, all entitled "Systems and Methods for Tissue Stimulation in Medical Treatment", said application also claiming benefit of 60/593,521 filed Jan. 21, 2005, entitled "Systems and methods for treatment of epilepsy and other neurological and psychiatric disorders", and this application also claims priority of U.S. Provisional Application No. 60/766,499 filed Jan. 23, 2006 and incorporates all of these applications herein in their entirety.

The invention is generally directed to treatment systems and methods used to guide stimulation treatments and includes providing, in both responsive and non-responsive manners, roving stimulation signals used by implanted or external stimulation devices such as magnetic stimulators. The stimulators can induce electrical fields, gradients, and currents in the brain or body of a patient, and can be used in the treatment of medical disorders such as neurological, movement, and psychiatric disorders, or other disorders of the brain or body, and is particularly relevant to reducing the incidence of epileptic seizures.

BACKGROUND

The measurement and modulation of brain electrical activity have been investigated for close to a century. In general the lower-frequency endogenous potentials (e.g., 1-10 Hz) have been linked to inhibition and suppression, and are more prevalent during diminished arousal levels and sleep, while a shift to higher frequency activity, such as beta (e.g., 12-30 Hz) and gamma (e.g. 30-80 Hz) band activity, is associated with increased arousal and excitation. Neurostimulation which alters these endogenous frequencies in areas of the brain can be used to modulate the relative arousal level of various brain structures, in the treatment of disorders. Different brain disorders can be associated with deviations in the activity of a particular region of neural tissue compared to those of healthy brains, and stimulation may attempt to normalize or compensate for this activity. Neurostimulation may utilize a wide range of signals such as pulsatile or sinusoidal waveforms, which can be provided using low or high repetition/modulation rates. Recently, slower frequency neurostimulation has shown promise in the treatment of different disorders. Although therapy for a disorder may be obtained by neurostimulation, side-effects due to disruption of endogenous activity may also result. These can include alterations in processes related to learning, cognition, memory, and attention. Certain side-effects are more likely with neurostimulation signals which have a primary component which occurs at the same frequencies as endogenous signals, especially below 15 Hz. Adjusting characteristics of the stimulation signal, in relation to those of endogenous signals, for example, in order to match or avoid matching certain characteristics of the endogenous signals, may be increasingly important when providing therapy at these lower rates of stimulation. Another solution is to rove a parameter of the neurostimulation signals, such as the dominant frequency of pulse repetition rate, to such an extent that a particular type of stimulation does not continuously interfere with endogenous potentials. Unlike conventional neurostimulation protocols which set the stimulation parameters and then provide stimulation in a consistent manner, the current invention describes different methods of roving the stimulation parameters so that the stimulation signals alternate regularly over time.

Roving of stimulation parameters can be used to address a number of well known factors which impede treatment. For example, since most neurological disorders comprise a cluster of symptoms roving can be designed so that the stimulation treatment is provided across time in a sequential manner in order to intermittently deter the emergence of different symptoms. Further, similar symptoms may be related to different disorders, and have different underlying biological causes, each of which can be addressed by roving the stimulation parameters to using parameters which have been empirically shown to decrease these symptoms in question. There may be different mechanisms behind different symptoms of a disorder which require relatively different treatment approaches. The treatment of epilepsy, provides an illustrative example, since therapy has been successfully provided using both slow (e.g. 1 Hz) and fast (e.g. 50 Hz) stimulation rates. Neurostimulation at lower and higher frequencies may work via several mechanisms such as depolarization blockade, synaptic inhibition/depression, and modulation, such as entrainment or suppression of endogenous activity and modulation of brain networks. The correct adjustment of neurostimulation parameters for the treatment of a wide array of disorders may depend upon multiple factors, and a consideration of the advantages of different stimulation strategies and signals is important. Strategies which alternate, rove between, or synchronously provide two or more stimulation signals may serve to modulate the brain in different manners and likely offer a number of advantages over chronic stimulation with a particular signal.

SUMMARY

Illustrative embodiments demonstrate a number of methods which can be used for improving stimulation to treat various disorders. Roving strategies are described for decreasing the risk of using ineffective stimulation parameters, stimulating non-target tissue, development of tolerance to stimulation, and other unwanted side-effects.

Roving methods are described for selecting, and subsequently implementing, useful stimulation parameter values. Selection of parameter values occur based upon their ability to provide therapeutic benefit, as may be reflected in good test scores. In one embodiment of the method, a treatment parameter value is systematically varied, and sensed data are collected, processed, and scored, in order to determine what parameter values most successfully led to desired treatment effects (e.g., test scores that met a threshold criteria). These successful parameters can then be selected (using ranking and/or meta-analysis of test scores) and relied upon during treatment. In the treatment of epilepsy, for example, a value of a stimulation parameter, which is associated with the frequency content of the neurostimulation signal, is roved. This produces signals with spectral energy that varies across a specified frequency range (e.g., either carrier frequencies or modulation frequencies are iteratively varied). The sensed data are then processed to determine the stimulation parameter values that led to decreased seizure scores, and the values associated with the lowest scores may then be selected to be used in treatment (e.g. FIG. 12). Treatment programs can alternate between two or more stimulation parameter values to define stimulation signals. Further test scores can be selected which reflect decreased seizure activity for different types of seizures. It is a feature of the invention to utilize a treatment program which provides at least two stimulation signals that are designed to treat, or designed in relation to the characteristics of, two different symptoms of a disorder. Test scores may also relate to different symptoms of other disorders, such as rigidity and tremor as is often seen in movement disorders.

The invention provides methods and systems for functionally increasing focal activation. Partial signals are used which summate to create therapeutic vector signals. The stimulation parameter values for different sets of partial signals can be chosen and tested automatically, or by a physician or patient. Sets of partial signals which provide therapeutic stimulation while not producing, or minimizing, unwanted side-effects can be selected for treatment ("successful parameter values"). The selection of treatment protocol parameters and treatment signals including partial signals, or vector signals, can be determined according to methods described herein. Partial stimulation signals of different temporal and frequency compositions can be selected to increase the transmission of the stimulation signal, to provide excitatory or inhibitory stimulation, and to induce desired temporal patterns of activity within different areas of tissue. Roving of the stimulation parameters of partial signals can be accomplished so that the characteristics of the vector signals are either approximately held constant, or are also roved in a fashion that is either similar or dissimilar to the changes which occur in the partial signals.

The stimulation methods may occur without relying upon sensed data obtained from sensors. Alternatively, stimulation parameter values may be adjusted based upon "sensed activity" which is patient input (e.g., via an external patient programmer that communicates with an implanted device. This input can be obtained using semi-automatic algorithms or manual methods which are completely under control of the patient. Sensing may occur as therapy progresses or only during assessment periods, such as may occur in the presence of a medical practitioner. When the sensed activity concerns neural processes related to cognitive phenomena such as attention and learning (e.g., hippocampal activity), the stimulation signals which modulate this activity may also produce undesirable side-effects. Interference in endogenous activity may be diminished using roving. For example, the pulse repetition rate of a stimulation signal can be intermittently roved between frequencies that are within and outside of the frequency range that characterizes a patient's theta activity.

While neurostimulation, especially with respect to treatment of seizures, is emphasized in some of the material here, the treatment of other disorders of the brain and body are also described and are no less central to many of the advantages of the inventive principles. These stimulation techniques can be applied to the brain during neuromodulation for the treatment of disorders, such as, epilepsy, or can be used for the treatment of disorders such as cardiac disorders which can be treated via central nervous system (CNS) targets or by direct stimulation of cardiac tissue. The systems and methods of the invention can also be applied to the vagus and other nerves related to modulation of the central and peripheral systems (e.g. unilateral or bilateral stimulation of the trigeminal nerves), and can be directed towards the tissue of the spinal cord. When used with transcranial magnetic stimulation, stimulation methods can be used to promote and modulate sedation and anesthesia. Other advantages, novel features, and further scope of applicability of the invention will be described in the following illustrations and description.

BRIEF DESCRIPTION OF THE DRAWINGS

For the purpose of illustrating the invention and its advantages, there is provided a detailed description and accompanying drawings of embodiments which are presently preferred. In illustrations of the methods, when arrows indicate iteration (i.e., a return from later steps to prior steps), this iteration is understood to be a preferred embodiment, and executing the steps a single time may also be an option. Steps which occur sequentially may also be realized approximately concurrently, or may be repeated several times (e.g., in order to provide a statistical estimation of a measure by computing the mean) prior to the next step occurring. It is understood that the invention is not intended to be limited to the precise arrangements, scales, and instruments shown, wherein:

FIG. 2a shows a schematic illustration of a system designed to create partial signals to be used during neurostimulation, which can be implemented in the stimulation subsystem;

FIG. 2b shows a schematic representation of a method of using a system designed to create partial signals that are used during neurostimulation;

FIG. 5a shows a flow diagram of a method designed in accordance with a preferred embodiment of the present invention, wherein two partial signals are created by adding interference signals to a low frequency base signal;

FIG. 5b shows a flow diagram of a method designed in accordance with a preferred embodiment of the present invention, wherein two partial signals are created by adding interference signals to a high frequency base signal, and further includes a step of adjusting the signals;

FIG. 6 shows a flow diagram of an alternative method designed in accordance with a preferred embodiment of the present invention, wherein two partial signals are created by deconstructing or modifying a base signal, and wherein these partial signals are re-assigned to different contacts at different moments in time;

FIG. 7 shows a flow diagram of another method designed in accordance with a preferred embodiment of the present invention, wherein the stimulation signal is roved across a frequency range, or alternated between at least two frequencies, during the therapy;

FIG. 8 shows a flow diagram of another method designed in accordance with a preferred embodiment of the present invention, wherein sensed data indicate the proportion of time during which 2 or more medical events occur, and stimulation occurs based upon this proportion;

FIG. 9 shows a flow diagram of another method designed in accordance with a preferred embodiment of the present invention, wherein the stimulation signal is temporally distributed across a number of stimulation locations;

FIG. 10 shows a flow diagram of another method designed in accordance with a preferred embodiment of the present invention, wherein the stimulation signal is modified to either positively or negatively reinforce endogenous rhythms of sensed data, and which may be applied with a specified phase or temporal relationship;

FIG. 11 shows a flow diagram of another method designed in accordance with a preferred embodiment of the present invention, wherein the stimulation signal is selected, created, or created from the sensed data, to either positively or negatively reinforce endogenous rhythms, and which may be applied with a specified phase relationship;

FIG. 12 shows a flow diagram of another method designed in accordance with a preferred embodiment of the present invention, wherein the stimulation signal is adjusted, based upon comparing test data to previously sensed data, to provide improved therapeutic benefit;

FIG. 13 shows a flow diagram of another method designed in accordance with a preferred embodiment of the present invention, wherein the two or more parameters of the stimulation are selected or adjusted, based upon evaluation of sensed data, to provide improved therapeutic benefit;

FIG. 14 shows a flow diagram of an alternative method designed in accordance with a preferred embodiment of the present invention, in which rather than relying upon the creation of new stimulation signals, stimulation signals are modified before being applied in order to alter the stimulation signals at different moments in time; and, FIG. 15 shows a device for providing transcranial magnetic stimulation to a patient.

DETAILED DESCRIPTION

Figure 1:
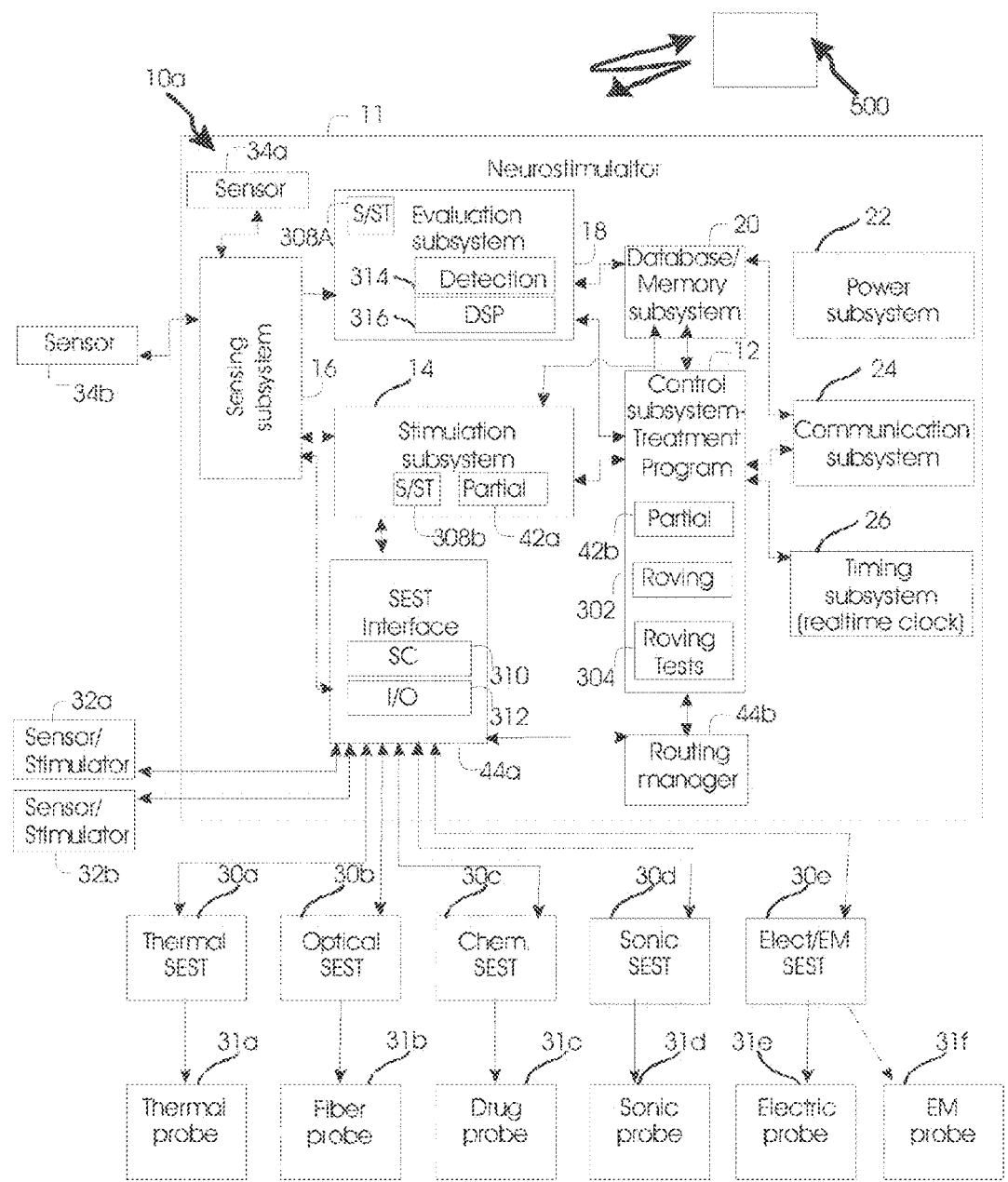
FIG. 1 shows a schematic illustration of one embodiment of a neurostimulation system which can be used in the current invention.

FIG. 1 is an overall block diagram of the implantable device 10a used for providing treatment-related functions such as stimulation which can occur independently or in response to sensing and evaluation of data. In housing 11 of the device 10a several subsystems and modules work together to provide therapy. 'Modules' may be software subroutines and hardware components which are designed to achieve features of the invention. The device 10a may be configured simply to provide stimulation treatment or may provide for both sensing and stimulation (SEST) operations. The control of sensing, evaluation, and stimulation is accomplished by the control subsystem 12, which operates according to the treatment program 300. The control subsystem 12 communicates with and controls the sensing 16 and stimulation 14 subsystems so that these perform SEST operations.

The control subsystem 12 implements the treatment program 300 which includes the subroutines, algorithms, protocols and protocol parameter values needed to accomplish calibration and operation of the system 10a in the provision of treatment. The treatment program 300 can select various treatment protocols including the sensing, evaluation and stimulation protocols, and the respective parameter values, which are used by those subsystems. The control subsystem 12 is functionally connected, either directly or indirectly, to all the other subsystems and components within the device 10a, for achieving control and communication operations inherent in providing therapy. The treatment program 300 allows the control subsystem 12 to control and coordinate all functions carried out by various subsystems of the system 10a, 500.

At various times prior to, during, or after implantation, the treatment program 300 can be programmed to select or adjust treatment protocols in relation to predetermined times of day and durations (e.g., time since the last stimulation protocol was selected). Additionally, the patient may use a patient programmer 500 to select and adjust the treatment program's protocols 300. The control subsystem 12 can include roving module 300 which contains algorithms and parameters for implementing roving-based treatment, and a roving test module 304, for allowing testing, evaluation of roving test results, selection of successful roving parameter values, and storage of information related to roving test results. The control subsystem 12 can also contain a partial module 42b that is used in the creation, calibration, testing and adjustment of partial signals. The partial module 42b collaborates with partial module 42a of the stimulation subsystem in order to operationally generate the partial signals according to methods described herein.

The various treatment protocols and their parameter values are stored in the memory 20, which is preferably realized as a programmable and querieable database. The control subsystem 12 can access this memory 20 to select information such as "candidate protocol parameter values", self-norm data values, customizable stimulation routines and protocols, treatment threshold values, and other settings and subroutines which are stored and retrieved during the provision of therapy. The control subsystem can also utilize the memory 28 to keep a record of the results of evaluation subsystem 18 such as past detected events, features and statistical measures computed upon these features, self-population normative data, and other information related to the evaluation of sensed signals (e.g., event occurrences, durations, times and counts). The historical record may also contain events marked by the patient using the external programmer 500 and a record of stimulation treatments. This historical record can be used to evaluate, and may cause the treatment program 300 to adjust, therapy based upon this evaluation. For example, if analysis of this "event history" shows a recent increase in event incidence which is above a pre-specified value, or which meets a statistically-based treatment criterion which indicates a significant increase in events over time has occurred, then a change in stimulation protocol may be implemented according the treatment program. A change in stimulation protocol can include a change in the roving stimulation parameters values, a change the rates of roving, times between roving operations, or may cause a change in the characteristics of the partial signals which are used.

The memory subsystem 20 can contain test results from roving tests, test results relating to the efficacy of combinations of partial signals, as well as different sets of roving and partial signal parameter values. Data stored in a memory subsystem 20 may be retrieved by the patient's physician or by the patient through the communication subsystem 24. A software operating program run by the external patient programmer 500 allows the physician to request the sending of historical events and data including sensed information before, during, and after each detected event, as well as specific information relating to the detection of each event.

The device 10a may provide therapy using stimulation alone or using both stimulation and sensing operations. The sensing subsystem 16 is capable of being physically and electrically coupled directly to a plurality of sensor probes 34a, 34b. In one variation, the sensor 34a can be an accelerometer which is within the housing 11 and sensor 34b can be SEST-conduit which is a multi-stranded electrode lead having a plurality of contacts at its distal ends and is attached at its proximal end to a sensor attachment means in the housing 11.

For most SEST-operations the SEST-signals will be transduced, processed, conditioned, and routed by the SEST-interface 44a. The SEST-interface operates under control of the sensing and stimulation subsystems to accomplish therapy operations defined by the treatment program 300. For example, the sensing and evaluation subsystems 16, 18 can operate the SEST-interface 44a in order to evaluate the incoming signals according to the parameters of the sensing protocol, and the same is true for the stimulation subsystem 14, with respect to the generation of the stimulation signals. The SEST-signals are guided between the SEST-probes 31, 32 and the sensing 16 and stimulation 14 subsystems under control of the routing manager 44b.

The SEST-interface 44a not only routes incoming signals (from sensors) and outgoing signals (to stimulators) to selected SEST-probes but also conditions signals using a signal conditioning (SC) module 310 that provides any operations not present in the SEST subsystems 14, 16 including but not limited to amplification, for control of, polarity, anode/cathode/ground/and isolation assignments, current and voltage regulation, analog-to-digital conversion, digital-to-analog transduction, and charge-balancing functions. Low level multiplexing, port/bus communication, address and control line operations, and routing functions are accomplished by the I/O module 312. The SC module 310 can contain programmable amplifiers, filters, and digital and analog signal processing (DSP/ASP) circuitry. Circuitry related to impedance testing and calibration can also be provided to assist in implementing the intended stimulation and calibration routines. The SC module 310 contains modules for allowing the stimulation subsystem to create modulated signals such as amplitude and frequency modulated signals, and to create carrier signals which are stable or which rove over time, and which may be bandwidth modulated to adjust the span of their frequency content. In general, the SC module 310 provides hardware and related operations that are required for a proper interface with tissue and which are not provided by any other subsystem of the device 10a.

The stimulation subsystem 14 and sensing subsystem 16 are capable of performing SEST-operations using a number of different types of SEST-modules 30a-e that communicate with SEST-probes 31a-e that are implanted in target locations. The SEST-probes 31, 32 are configured for either sensing or stimulation of tissue, or both. The SEST-interface 44a can communicate with, control, and provide power to SEST-modules 30 and SEST-probes 31 and can establish communication with either the sensing 16 or stimulation 14 subsystem. FIG. 1 shows a thermal SEST-module 30a (e.g., Peltier junction or thermocouple), an optical SEST-module 30b, a chemical SEST-module (which may include a reservoir and programmable pump) 30c, a sonic (including ultrasonic) SEST module 30d, and an electrical/electromagnetic SEST module 30e. Additional SEST modules 30 are also possible (e.g., additional visual, or tactile signals in order to provide somatosensory stimulation to locations other than the brain). The thermal probe 31a contains a SEST-element which can be a thermally conductive surface. The optical probe 31b contains a SEST-element and may have optical adjustment components such as a programmable aperture or biocompatible lens at its distal tip through which light is presented. The optical SEST-module 30b communication may include power, communication, control, and sensed signals that are sensed by the optical probe 31b which are relayed to the SEST-interface 44a, and then to subsystems of the device by the routing manager 44b. The optical SEST-module may also provide a light source to the optical probe 31b. The optical probe 31b can be a single optical sensor or can be several sensors. The chemical probe 31c may be a stimulation conduit which is a catheter that may or may not have valve devices for outputting drugs (used either alone or in conjunction with other types of stimulation including stimulation which can activate the drug) at specified stimulation output sites, as well as a chemical sensor. The sensors 34, SEST-modules 30 and SEST-probes 31, 32 may be located within the device 10a, or may be implanted elsewhere and controlled by the device, and may also deliver stimulation therapy themselves A SEST-probe may also contain processing circuitry for accomplishing the sensing and stimulation and for switching between the sensing and stimulation activities and for transducing the signals. In the various types of sensed data described herein (e.g., electrical impedance plethysmography, etc.) the data is often measured relatively, such as according to baseline measurements, rather than as an absolute value, and can also be adjusted (e.g., calibrated) according to measured variance so that the signals are meaningful. When SEST-probes 31 contain a plurality of contact elements, the SEST-modules 30 can be programmed so that stimulation is applied according to roving and partial signal methods. Some probes that may be used by the device have been listed in U.S. Publication No. 2005/0277912 to John, which is hereby incorporated by reference in its entirety.

When used to treat seizures, at least one SEST-probe 31 can be situated in a brain region, in order to sense activity from an epileptogenic region, a spike focus, a focal functional deficit, an irritative zone, a structure of the limbic system or the temporal lobe, or any structure which is characterized by abnormal electrical or neurochemical activity. Stimulation can occur using a SEST-probe 31 configured to stimulate the brain, and/or cranial and vagus nerves. When used to treat pain, one SEST-probe 31 can be in the brain, spine or peripheral nerves, to detect symptoms related to pain, and the stimulation electrodes can be located to stimulate target areas such as the spine. When the disorder is pain the particular symptom types can be related to the type, location, size, quality and duration of pain symptom. Although pain symptoms can include physiological and biological correlates of pain, the symptoms can be detected and quantified according to patient input via the patient programmer 500. When used to treat tremor or movement disorders, a SEST-probe 31 can be located in a limb manifesting symptoms of the disorder, proximate to the motor or pre-motor cortex, or in a region of the brain having, for example, excessive synchronous activity related to the frequency of a tremor. When used to promote chemotherapy, a drug SEST-probe 31c can be in a region near a tumor.

The sensing subsystem 16 senses data according to the parameters of a sensing protocol. Sensed data may be comprised of ongoing activity or activity related to stimulation (e.g., a short post-stimulation blanking period may be used to avoid saturation of the amplifier when both sensing and stimulation occur in the electrical modality). Sensed data may include, but are not limited to, EEG data, neuronal recordings (e.g., single neuron recordings, nerve potential recordings, local field potential recordings), ultrasound data, oximetry data, optical sensing data, blood pressure recordings, impedance measurements, measurements of temperature and acceleration, measurements of emitted or absorbed radiation (e.g., infrared spectroscopy measurements and spectrophotometric measurements), and combinations thereof.

The evaluation subsystem 18 processes and evaluates sensed data according to the parameters of an evaluation protocol. The evaluation subsystem 18 can detect events, using detection module 314, defined by a treatment program 300 that are related to one or more symptoms of a disorder and can use the detection module 314, and the detection of events may occur using a waveform analysis method as is described in U.S. Pat. No. 6,480,743 to Kirkpatrick et al. It contains a digital signal processing DSP module 316 for processing of the sensed data using temporal, spectral, and time-frequency analysis, modeling, feature detection and quantification, and pattern matching. The DSP module 316 can be used by the detection module 314 to detect selected events (and quantify selected features) such as epileptiform, tremor, or other activity related to various types of symptoms of the disorder being treated. The evaluation subsystem 18 can include compensation for variations in heart-rhythm (e.g., heart rate may be measured by taking average or peak values over several measurements), activity level, body position, and time of day.

When the sensor utilizes one or more sensor for measuring intracellular activity, evaluation of sensed data can also include spike count, integrated voltage, spike histogram, envelope of activity, spike-to-burst ratio, or average spike frequency. Processing of sensed data can provide scores, an index related to measuring chaos, complexity, various Hjorth parameters, equations including weighted scores from previous results, and other types of measures and results. In one example, the analyses of the sensed data is altered by at least one of the prior events which has been detected, or scores which has been generated, which triggered an alteration in the evaluation protocol. Evaluation of sensed data can occur in an evaluation subsystem, can occur in a distributed fashion, as needed, by the other subsystems of the device 10a, and can also occur in the external patient programmer.

The evaluation subsystem 18 can be used to measure current therapeutic benefit by comparing features of the current data to treatment criteria, such as threshold values for the size or number of occurrences of electrophysiological signatures of tremor or seizure. The evaluation operations can be statistically based and utilize multivariate equations, logic trees, and can rely upon logical operators, to combine evaluation of different conditions used to assess the data. For example, an event may be detected "if A>X and B.about.=1", where A, B are values of features computed from sensed data, and X is a threshold defined in the evaluation module. Sensing and evaluation systems which may be used in the current invention are described in U.S. Pat. No. 6,066,163, and are well known in the art.

The treatment program 300 can use the results of the data analysis of the evaluation subsystem 18 to adjust the stimulation protocol 22 and select stimulation parameter values that are used to define the stimulation signals. In some embodiments, evaluation of sensed data can entail comparing incoming signals to reference values (e.g. self-norm values stored in the database 20) according to one or more treatment criteria, determining test results (e.g., positive or negative results), and modifying the stimulation protocol based upon these test results as is described in the methods herein.

Generally, evaluation of sensed data can be used to adjust therapy, or provide closed-loop or other type of responsive treatment. Closed-loop implementations can use sensed data of one modality to provide stimulation in another modality. Evaluation of sensed electrical EEG data may be used to select optical stimulation signals and thereby provide "multimodal physiological" control of stimulation parameters. The evaluation subsystem contains a detection module 314 with algorithms for identifying medically relevant events, which can lead to stimulation treatment according to the therapy program of the control subsystem. In one variation, electrographic signals are received by SEST conduits, such as electrodes, and a detection subsystem 314 includes an EEG waveform analyzer that can implement both time and frequency analysis for detecting characteristics of the waveforms that have been defined as requiring adjustment or provision of stimulation (e.g., as described in U.S. Pat. No. 6,016,449 to Fischell et al. and U.S. Pat. No. 6,810,285 to Pless et al., which are hereby incorporated by reference in their entirety). Similar detection algorithms may be applied to the analysis of other types of waveforms received from other types of sensors. In addition to chronic stimulation, responsive cortical neurostimulation may be a safe and effective treatment for partial epilepsy (Kossoff et al., 2004). Responsive neurostimulation can lead to less tolerance and side-effects since the stimulation is not chronic. Some have suggested using non-responsive neurostimulation with the addition of responsive neurostimulation, in order to deter seizures which were not prevented by the first type of stimulation.

In other embodiments, the treatment program 300 can control the evaluation of sensed data to provide responsive treatment to events which are detected. The control subsystem 12 can operate the DSP 316 module to perform signal processing and control law implementation. A type of responsive therapy can be achieved using control-law algorithms derived from characteristics of sensed data that provide control signals, as implemented by known methods (e.g. US20050240242) which incorporate disease state estimators, proportional control laws, and other tools of control theory.

The evaluation of sensed data can entail evaluation of spatial and spatial-temporal characteristics of sensed data by the spatial/spatio-temporal (S/S-T) module 308A. When this module indicates a specified spatial pattern of neural activation (e.g., the area of tremor activity spreads beyond a threshold value) has occurred then this may be defined as a signature of a type of symptom for which treatment has been defined. By calculating the incidence of different symptoms, the treatment program 300 can calculate the relative rates of different symptoms and can adjust the parameters of the roving module 302 so that stimulation with 2 or more parameter values related to the two or more symptoms may occur proportionately. In another example, the detection module may detect a type of abnormal activity at a sensor near a seizure focus, and over time it may both increase in amplitude and also be increasingly sensed by sensors in more distal locations (indicating either movement of the source or change in orientation of the dipole). This pattern of activation may be related to a specific symptom of the disorder (i.e. a specific type, time of occurrence, duration, location, size, and count of seizure activity) and may require a unique stimulation treatment that is provided when the activity is detected according to a different spatial or spatial temporal pattern. Since roving of the parameters of the stimulation treatment may occur using a strategy where different values are used proportionally to the incidence of symptoms, recognizing different symptoms by spatial-temporal profiles of one or more types of seizures (where each is considered as a different physiological symptom) provides essential information.

The S/S-T module 308a may also be used when evaluating the strength of partial signals which are emitted by stimulators at one location and sensed by sensors at a different location. The S-ST module 308a of the sensing subsystem, can operate in conjunction with the S/S-T module 308b module of the stimulation subsystem in order to perform testing of various partial signal combinations as occurs in the method illustrated in FIG. 2b.

The evaluation system 18 and its detection module 314 may contain a plurality of evaluation and detection capabilities, including but not limited to analyzing measures derived from physiological conditions (such as electrophysiological parameters, temperature, blood pressure, neurochemical concentration, etc.) either jointly (e.g., electrical and optical data are combined to assess events) or in an independent fashion (e.g., electrical and optical data are each evaluated separately to assess events) so that different symptoms of the disorder can be recognized. Different symptoms can also be defined in relation to user input indication of different symptoms, using the communication subsystem 24 which communicates with the external patient programmer 500.

When sensing is used in combination with stimulation, evaluation of sensed data can lead to responsive stimulation or adjustments in ongoing stimulation. This transition can be implemented for at least one of the partial signals, base-signals, or conventional signals that are used to provide stimulation. Sensed data can be processed using filters, where the band-pass and band-stop parameters are programmable, and where the center frequency and filter width can be adjusted, and the filter output can be used to adjust the stimulation signals. Multiple filters and signal processing routines can be used to create multiple stimulation signals or to quickly evaluate sensed data. For example, a bank of narrowband filters can be used to rapidly determine a measure which is the frequency of peak spectral power, so that this frequency can be assigned to a parameter value in order to shape the stimulation waveform. Additionally, adaptive filters, such as Kalman filters, or independent component analysis, can be used to track temporal or spectral characteristics of the sensed data signal. These characteristics can be used to derive a measure or a set of measures which are used to modify the stimulation signals. An evaluation of the sensed data can provide a measure which tracks the frequency with peak spectral power of one or more specified bands of power, such as the frequency of a tremor or seizure.

The stimulation subsystem 14 provides stimulation according to the parameters of a stimulation protocol. The stimulation subsystem 14 provides for creation and transduction of different pulses and other waveshapes which serve as the stimulation signals, and can include programmable signal generators. The stimulation subsystem 14 includes stimulation conduits which provide stimulation signals to SEST-probes. The stimulation subsystem 14 includes modules that enable the creation of partial signals 42a using methods such as those shown in FIG. 2a and FIG. 5a. The partial signal module 42a therefore permits subtraction of partial signals from vector (or 'base') signals, the addition of interference signals, analog-based modification of vector signals using specialized circuits of the SC module 310, and other methods. The provision of spatial/spatial-temporal patterns of stimulation and sensing can be accomplished by the S/S-T module 308a-b as may be required by different stimulation protocols unique to the device 10a such as roving stimulation which may optionally be accomplished in conjunction with partial-signal methods.

Similar to known devices, stimulation can be programmed to occur as a substantially continuous stream of pulses, on a scheduled basis, responsively using a predefined stimulation protocol or a protocol which is adapted based upon a characteristic (e.g., the size) of the measured data and of the detected events (e.g., using proportional control laws with minimum thresholds which do not output a control signal until a characteristic of an input signal reaches a specified threshold related to the detection of an unwanted type of activity), and in other manners dictated by the treatment protocol. In one variation, roving-based therapy may be performed by the system 14 in addition to, and independently of, responsive therapy. Stimulation can be provided to reinforce endogenous activity and can be applied with a selected delay to be primarily in-phase or out-of-phase with a sensed feature.

The control subsystem 12, under the direction of the treatment program 300, can use its communication subsystem 24 to communicate with an external patient programmer 500 and to implement SEST-operations using other sensors or stimulators which may be provided by other implanted devices, as the case may be. The communication subsystem 24 enables communication operations that are necessary for therapy. The communication subsystem 24 may include a telemetry coil (which may be situated outside of the housing of the implantable device 10a) enabling transmission and reception of signals, to or from an external apparatus, via inductive coupling. The communication subsystem 24 may also include an alarm subroutine, which may cause the communication subsystem 24 to send an alarm to the external patient programmer 500 or may send an alarm to an acoustic stimulator 30d of the device if it detects that something has occurred for which an alarm should be triggered. For example, if the power supply 22 falls below a specified level, or if error codes are generated by error detecting algorithms in the various subsystems of the device 10a. Additional sensors or circuitry may be provided to detect electrical shorts or fluid leaks between plug contacts of interface connectors, and to issue an alarm if such malfunction occurs.

A power subsystem 22 may include a rechargeable power supply that supplies the voltages and currents necessary for each of the other subsystems to function. The power subsystem may also contain circuitry for discharging or recharging the battery (e.g., via induction) and circuitry for indicating how much power is left, and this data can be sent to the memory subsystem 20. The timing subsystem 26 supplies substantially all of the other subsystems with any clock and timing signals necessary for their operation, including a real-time clock signal to coordinate scheduled actions and the timer functionality used by the detection subsystem 314 that is described in detail below.

While the subsystems and modules of the device 10a are shown in specific locations and have been described individually, they may also be provided in an integrated fashion. For example, the control, sensing, evaluation and stimulation subsystems may all be realized on a single customized chip that has been designed to accomplish the functions described herein. Further, although the memory subsystem 20 is illustrated in FIG. 1 as a separate functional subsystem, the other subsystems can utilize this subsystem 20 when these require various amounts of memory to perform their operations.

A plurality of 10a systems may also be used to perform one or more functions on neural tissue. Each 10a system may be operated independently, or may communicate to provide synchronized stimulation, for example, as may occur when a 10a system is implanted in the cranium of each hemisphere and delivers therapy to each, respectively. The implantable device 10a may also comprise a plurality of spatially separate units each performing a subset of the capabilities described above, some or all of which might be external devices not suitable for implantation.

As will be described, the implanted system 10a can be realized as an external transcranial magnetic stimulation (TMS) device 10b when the components are implemented in a TMS device. As an alternative treatment to direct electrical stimulation with implanted devices, external embodiments are also possible, for example using responsive and/or repetitive transcranial magnetic stimulation (rTMS). Repetitive TMS has been shown to decrease epilepsy with acute treatment sessions. For example, using treatment of 100 stimulations at 0.5 Hz, 5% below motor threshold, twice a week for 4 weeks resulted in a 70% decrease in seizure frequency compared with the months before stimulation (Menkes et al., 2000). Other reports have also related smaller decreases, on the order of 40%, using rTMS to treat epilepsy (Tergau et al, 1999). The rTMS treatment of various brain disorders offers advantages over direct brain stimulation in that invasive neurosurgical procedures are avoided. As in the case of continuous or repetitive stimulation, responsive stimulation, via TMS or direct deep brain electrodes, can be provided in accordance with the methods of this invention, including adjustment according to sensed activity, such as EEG rhythms. In line with decreasing the evasiveness of therapy, the stimulation advantages provided by the current invention can be obtained with treatment using direct stimulation via implanted electrodes, rTMS, stimulation of vagal or other cranial nerve tracts, or stimulation of other tissue and organs of the human body (e.g., the stomach or heart) which may be useful in providing treatment to various disorders.

FIG. 2A shows a schematic representation of a system designed to create and apply partial signals during stimulation. This system can be realized by the stimulation subsystem 14 and SEST-interface 44a. A signal creator 40 works with a partial signal creator 42 in order to create the partial signals, which are then routed 44 to be provided to selected contacts of stimulation conduits 32. The stimulation conduits are located sufficiently close to enable at least the partial summation of the individual fields of the partial signals, in order to approximately create a vector signal in at least a portion of a neural target. In one method the signal creator 40 supplies a base signal to a partial signal creator 42, which modifies the signal to create a number of partial signals. For example, by adding selected interference signals to the base signal, partial signals can be created so that their summation leads to a vector field which is approximately the base signal. The size and polarity, and even orientation, of the interference and partial signals can be adjusted, by the partial signal creator 42, based upon an algorithm which incorporates the spatial location, impedance, and orientation characteristics of the stimulation conduits (e.g., electrode contacts or optical outputs). The partial signals can be generated digitally using algorithms, or analog circuitry, or can be selected from a database 28 of predefined partial signals. Partial signal generation may also include information about the 3-dimensional positions of grounds and active leads as well as the approximate impedances, orientation (in the case of directional leads) and other relevant characteristics of the leads, which is stored in the database 28. The creator 42 can generate at least two partial stimulation signals based upon these calculations in order to produce approximately the desired electrical field summation signal in approximately one or more target tissue regions.

The partial signals may be directed to their intended stimulation conduits 32 by the signal router 44, which also may be realized within the stimulation subsystem 14 and which can contain SC components such as digital-to-analog converters, filters, amplifiers, switches, charge balancing and biasing circuits, and mutliplexors, each of which can be separate components or which can be embodied into a specialized microchip.

FIG. 2B shows a schematic representation of a method of using a system of the invention, such as that of FIG. 2A, that is designed to create partial signals. The first step is to create at least one stimulation signal 50 to be used during treatment. The stimulation base signal (e.g., a signal that has been selected due to its ability to provide a benefit such as symptom relief) is then transformed into two or more partial signals 52 which are provided at each of two or more contacts 54. A calibration method (including steps 54, 56, 58) can be used, from time to time, in which the partial signals are adjusted based upon data which is sensed concurrent with stimulation. For example, a calibration signal which may be at least one partial signal is used to stimulate contact set"i" of N contacts 54, and data are sensed at contact seer 56, where sets"i" and"j" each include at least one contact. The sensed data allows empirical measurement of the electrical field and can be used to adjust the partial signals 58 so that the actual field vector more closely approximates the intended vector field in 3-deminsional space.

Figure 3A:
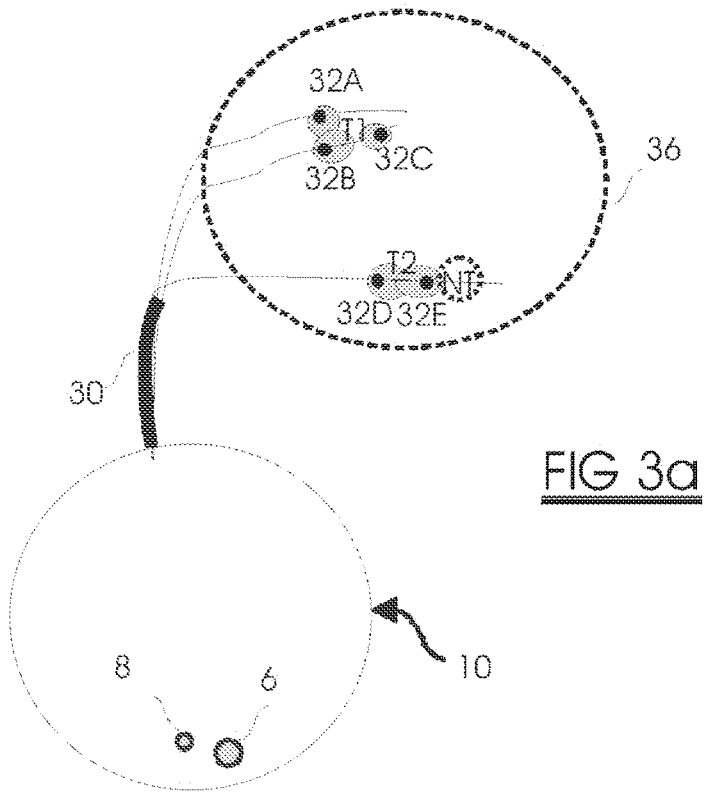
FIG. 3A illustrates an embodiment of an implantable stimulation system including a device having 5 electrodes that are implanted in the neural tissue of a patient.

FIG. 3A Shows a generic implantable stimulation device 10 that has a stimulation conduit which includes five electrical contacts (32A-E) that are implanted in the neural tissue 36 of a patient 38 (not shown). The implantable stimulator 10 contains sensing, control, signal generating and computational circuitry, a power supply, sensors and other components which are commonly found generically in implantable stimulators such as have been described in U.S. Pat. No. 6,066,163, US2002/0072770, & US2004/017089. The stimulator 10 may also be realized using the neurostimulators 10a and 10b shown in FIGS. 1 and 15. The stimulator device 10 can contain a general access port 6 which serves different functions in different embodiments. For example, the access port 6 can comprise a re-sealable septum which accepts a needle for replenishing fluids used in drug delivery, or the access port 6 can accept a control link from an external controller device 500. The device 10 can also contain a connection port 8 for connecting, for instance, to sensors 34 which can provide sensed data, or which can accept a signal from another implanted device for permitting two or more devices to collaboratively provide treatment.

In some of the described methods, stimulation parameter values relating to characteristics such as modulation rate are described as alternating or roving. This may occur independently for each of the one or more (partial) signals of each of the stimulation conduits 32. Accordingly, a first stimulation signal could rove from 20 to 25 Hz, while a second signal concurrently roves from 26 to 27 Hz. The temporal delay, phase, amplitude, or other characteristics of the stimulation signals at each electrode can be independently set in the stimulation subsystem 14. The specified delay, amplification, filtering, and other parameters used to adjust stimulation signals according to sensed data can occur according to treatment protocols and, in selective embodiments, can occur responsively or according to the implementation of one or more control laws.

Figure 3B:
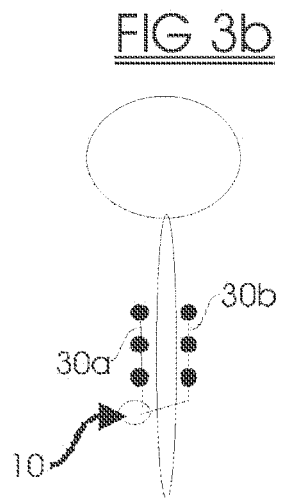
FIG. 3B illustrates an embodiment of an implantable stimulation system including a device having electrode sets that are implanted for spinal stimulation of a patient.

Stimulation can occur using two or more stimulation lead contacts (e.g., 32A and 32B) which stimulate at levels that would be subthreshold if provided individually, but which combine to produce super-threshold stimulation. Subthreshold stimulation can be used with stimulation leads whose fields summate to the extent needed for clinical efficacy (i.e. the fields of the partial signals combine to produce super-threshold characteristics) primarily in the region where neurostimulation is desired. In this example, contact 32A (black region) produces a field (grey region) that overlaps with the field produced by contact 32B, both of which produce fields as current travels to contact 32C, such that vector fields occur in target area 1 ('T1'). Bipolar contacts 32D and 32E may each be used to stimulate with a partial signal so that the overlap of their fields causes vector summation to stimulate target area 2 ('T2'). If an area of tissue is adjacent to a contact 32E, but is a non-target ('NT') area which produces side-effects when inadvertently stimulated, then even if the field produced by contact 32E should stimulate this non-target area, inadvertent stimulation of the non-target area may not lead to side-effects since the characteristics of the partial fields are different than those of the vector field (i.e., since the partial signals have a different spectral content then the vector field). FIG. 3B shows 2 sets of SEST-probes 31e and 31e' which contain sets of contacts located bilaterally and which may be aligned along the spinal cord of a patient when partial signals are to be used during treatment.

Figure 4A:
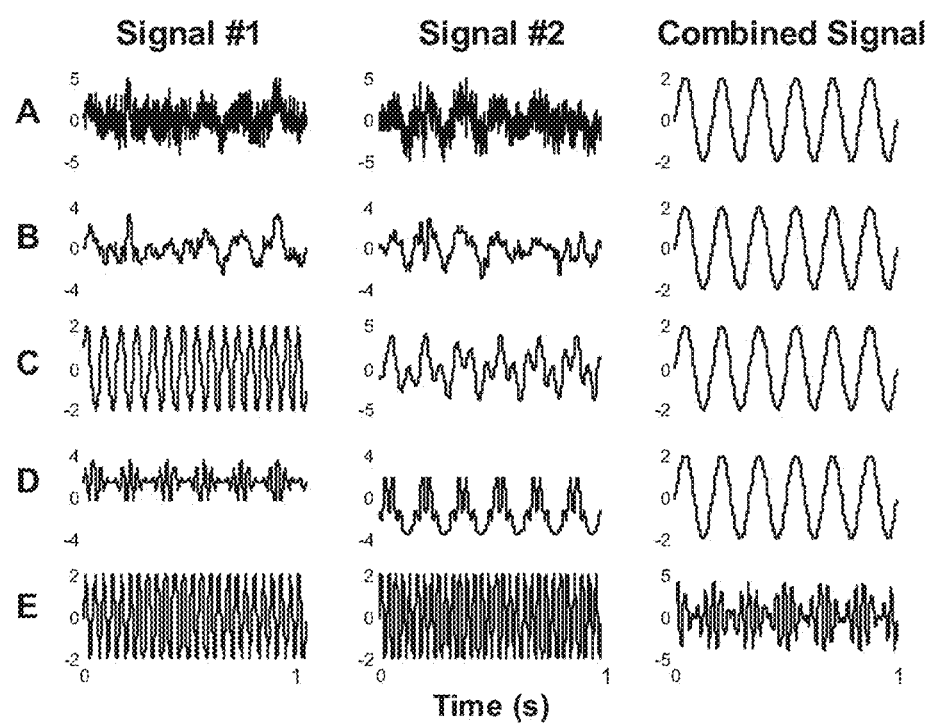
FIG. 4a shows examples of partial signals, where signal #1 and signal #2 are partial signals which can be combined to form a vector signal which is termed 'combined signal', and where the partial signals have a substantially different frequency content than the combined signal.

FIG. 4a shows examples of partial signals. Each signal is part of a set which can be provided at 2 or more different lead contacts. Each "set of partial signals" will combine to form a desired signal (a vector sum of the two partial signals) in or near the target tissue while stimulating with the partial signals outside of the target region. In row A, a wideband noise signal is shown in column 1, labeled "Signal #1", which when added to the "Signal #2" of column 2 will result in the "combined signal" shown in column 3. Rows B-E show other partial signals sets and their vector summation fields. The described methods for choosing stimulation parameters for conventional stimulation signals can also be applied to the selection of partial and vector signals. If a 'base signal' is selected as the combined signals of rows A-D (which are identical), each of the sets of partial signals can be tested, and the ones which produce therapy and reduced side effects can become successful stimulation signals. Only base signals and partial signals which are found to be successful stimulation signals may be selected to be included in the set of candidate stimulation signals which can be subsequently used during treatment.

Figure 4B:
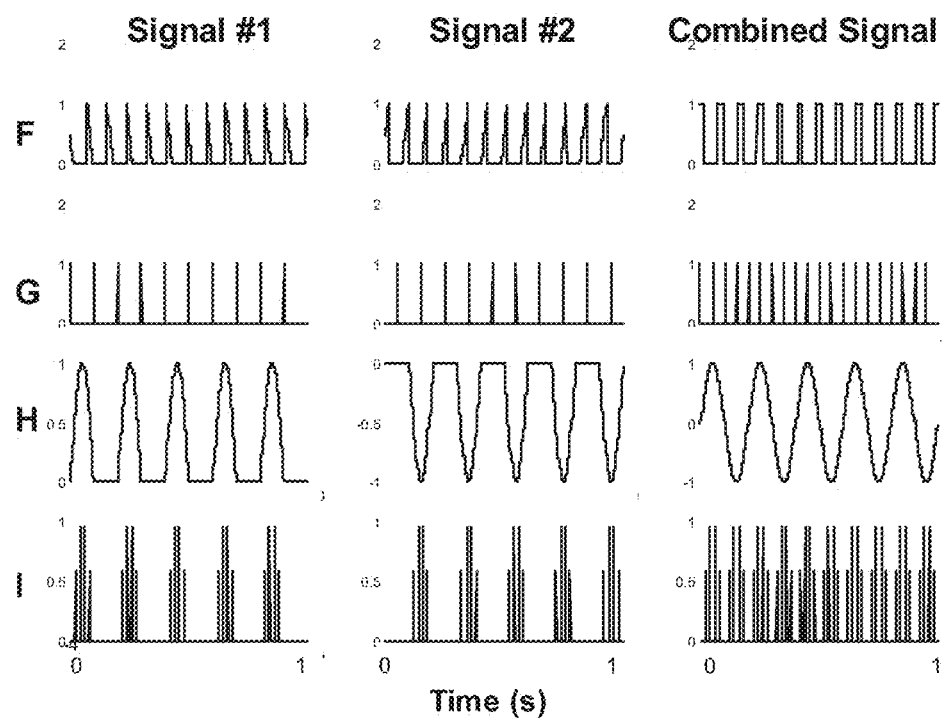
FIG. 4b shows alternative examples of partial signals and vector signals.

In FIG. 4B, additional examples of partial signals are shown having unique characteristics relative to the those of the vector signals of column 3, and offer advantages over known stimulation signals. In the first row of FIG. 4B, two saw-tooth pulses serve as the partial signals and these combine into a vector signal which is a square wave at the same frequency, having pulses of longer duration and different shape than the partials. Both the duration and shape of the partial signals can thus differ significantly from the resulting combined signals. Additional pulsatile signals are shown in rows G-1. In these cases, partial signal 1 was subtracted from the combined signal in order to obtain partial signal 2, as may occur in the partial signal creator 42 or related methods, e.g., steps 52, 82, 92. Among the various advantages, the signals in Row G combine to provide a vector signal which is faster than the partials, Row H combines single polarity waveshapes to create a bipolar vector waveshape, and Row I results in a pulse train of rate 2N, where the partials are each set to N, due to the phase relationship of the signals.

Partial signals which are applied to the non-target region can be selected as those which are unlikely to stimulate that area in unwanted manner. A sufficiently fast carrier frequency may affect neural tissue only at the onset of a train because it exceeds the chronaxie of the tissue and is thus functionally "invisible". In contrast, various ranges of high frequency stimulation (e.g., 1-6 kHz range) can both excite or block neural activity (Tai et al 2005). Modulation of a carrier signal which freezes, inhibits or excites a neural target can be useful in providing very specific entrainment, because this will oscillate with the modulation envelope (e.g., with the amplitude or frequency modulation). Additionally, when using a pulse train, pulse shape and/or duration can be set, relative to its current, voltage, inter-pulse-interval, or frequency so that the partial fields fail to entrain, or produce side-effects in the NT area, while the vector field contains pulses that are entraining (e.g., FIG. 4B).

Stimulation signals can be provided to both mono-polar and bi-polar stimulation conduits. When generated by mono-polar leads, these may stimulate as cathode or anode and may supply stimulation in conjunction with a further lead that, for example, serves as ground. Each electrical contact may be a ground, isolated, mono-polar or bi-polar with respect to anode/cathode assignment. When operated in a bipolar mode, one of the lead contacts can serve as a ground or opposite polarity relative to the other contact. Alternatively, the housing of the stimulator 10 can serve as anode, cathode, ground or may be floating. Other combinations of polarities are possible as well, for example the shell of the stimulator 10 can be divided into different sections which are electrically isolated from each other, and when more than one stimulator 10 is used, each may have a shell with a different electrical function, as may occur when the methods are implemented in stimulators such as the BION™, or a BION™ network. When multiple stimulators are used to provide the partial signals, these may have their grounds and power-sources connected to provide a common ground or power-source, although these may also be electrically independent.

Partial signals can also be created by the method illustrated in FIG. 5A, and comprises the step of creating a low frequency base signal 60 which is intended as the vector field signal, created by the summation of the partial signals in approximately the target tissue. The low frequency signal is added to a 1 st interference signal 62a to create a first partial signal, and then added to a 2.sup.nd interference signal to create a second partial signal 62b, and this process is continued until all the partial signals are created. The partial signals are then each applied to a selected contact 74. Step 74 can occur continuously, repeatedly, responsively, or according to alternate strategy as dictated by the treatment program. The partial signals can be re-assigned to the same or different contacts in subsequent iterations, after appropriate modification for electrode geometry, impedance, etc. Additionally, as indicated by the arrow from step 74 to step 60, this process can be repeated if the low frequency base signal or the partial signals require replacement, for example, as dictated by the treatment program 300. In FIG. 5B, a method is shown where a base signal with high frequency spectral content (e.g., a pulse train, paired-stimulus waveform, or arbitrary waveform) is created 76, and the interference signals are added to this signal 78a, 78b, to create partial signals that are applied at the contacts 74. A further method of providing the partial signals is shown in FIG. 6. The first step is to create a base stimulation signal 80, then create 2 or more partial signals 82a, 82b by modifying the base signal. Partial signals can be created by distributing the base signal spatially and/or temporally (possibly having some durations of overlap) across the different contacts, and then applying each partial signal to a unique contact 74. As the figure shows, the steps 80, 82 and 74 can be repeated in a loop to provide adjustment of the partial signals and/or base stimulation signal. If the stimulation signal is to remain constant and only the partial signals are to be adjusted then only steps 82a, 82b and 74 need be accomplished. All three steps can occur approximately simultaneously and continuously. After a specified amount of time has elapsed 26 the contacts for the first and second partial signals may be switched (e.g., step 84 of FIG. 6). In one embodiment, after a specified duration, the signals used at lead contact 1 become signals for lead contact 2, and vice-versa.

When the stimulator 10 is an external TMS device, instead of contacts the stimulation is produced by TMS coils which induce magnetic fields in the brain, and the re-assignment of partial signals may be even more important: unlike implanted electrodes, the fields will alter the activity of significantly larger portions of tissue outside of the target area. When more than 2 partial signals are needed, steps 82a and 82b, for example, are extended to steps 82c, 82d, etc to create these additional signals.

In a further embodiment, the creation of partial signals can occur by processing the base signals according to an algorithm. As is shown in FIG. 14, the stimulation signals can be created 90 and then these base signals can be processed 92, for example, by algorithms or processes implemented digitally or in analog form, in order to produce modified partial signals 94. The process can utilize a filtering algorithm which can iteratively filter the stimulation signals with different band-pass filters in order to create unique, and even spectrally orthogonal, partial signals which will combine to approximate the base signal.

Stimulation with Modulated Carrier Signals.

There are several "technical" problems which are encountered when providing neurostimulation, in the treatment of a disorder. Regardless of whether the stimulation signal is one of low or high spectral content, the signals which provide the best therapy, may not be optimal with respect to stimulation of issue. While certain stimulus waveforms may be good for treatment, these may be less well suited for transmitting energy from the electrodes to tissue, and subsequently through tissue itself. An approach to optimizing the desired effects of stimulation is to construct a "carrier signal" which may be comprised of an oscillating carrier at some high frequency, Fc(H), which is modulated by some lower frequency Mf(L) or contour Mc(L). In a preferred embodiment, the contour of the modulation waveform itself may be determined by sensed data, and/or may be a sine wave, pulse pattern, ramps of a specified rate of change of amplitude, or any arbitrary waveform. Changing the Fc while maintaining a constant modulation function may increase energy transmission, entrainment or selective entrainment of a neural target. These methods permit increased stimulation efficacy, by tailoring the Fc and Mf characteristics. More generally, a first characteristic of the signal is selected to provide therapy, and a second component of the signal is adjusted and provided in order to provide a secondary benefit such as decreasing a side effect or increasing energy transmission.

In some situations, it is advantageous to adjust the modulation envelope while the carrier signal (which may be a frequency, or band-pass noise, pulse train, etc) is maintained. In other situations, the modulation function should be held constant while the carrier signal is maintained. Alternatively, both may be adjusted in order to provide a therapeutic benefit such as better entrainment of tissue. In one method, a first characteristic of the stimulation signal such as a modulation rate may be selected based upon a first therapeutic benefit such as symptom relief, and is then held constant. A second characteristic of the signal, such as the carrier signal may then be roved, adjusted, or alternated in order to provide a secondary advantage, for example, increase the transmission of the signal through tissue (possibly then permitting a signal with decreased current or voltage to be used), decrease side-effects, or increase the level of entrainment of the stimulated tissue. The sensed data may be used it to determine carrier, envelope, or modulation rate of the stimulation signal, while a different characteristic of the signal is adapted to provide improved therapy.

For all the types of stimulation signals which are described in this specification, the stimulation signal can be provided with, or spectral content can be assessed, using the signals as described or using their fully or partially rectified counterparts. It should also be noted that a non-rectified amplitude modulated signal, does not have energy at the rate of modulation. The spectral energy of a modulated signal occurs at different frequencies depending upon the carrier signal. For example, an amplitude modulated signal has energy at the carrier frequency ($C_F$ and at sideband harmonics which occur at $C_F$+/−the modulation rate ($M_F$). Only by rectifying a signal will spectral energy appear at the frequencies of the modulation envelope. Generally, the neurons in the target tissue will become entrained by the modulation envelope, while the different carriers which may be used will act to entrain different neuronal populations and to transfer the modulated signal with different amounts or degrees of efficiency. Accordingly, the spectral content of the rectified energy of the stimulation signal may better reflect the spectral content of the evoked activity. In one embodiment, signals having rectified spectral content of between 0.5 and 20 Hz are used, although the signals themselves are centered around zero to avoid issues related to the application of D.C. and non-balanced stimulation signals.

The width of the spectral content of the stimulation signal may also be a parameter that is adjusted. Modulation of neural tissue using a narrow-band (e.g. 5 Hz) stimulation signal rather than a pure carrier wave (or pulse train) may entrain a greater proportion of neurons, where the width of the band-pass is adjusted to provide maximum entrainment. Additionally, in order to increase therapeutic efficacy, the stimulation signal may not return to, or cross zero, on every cycle, but rather can be biased. The second characteristic can be related to adjusting for a specified and desired level of positive or negative DC shift.

Generation of stimulation signals form sensed data can rely upon one or more fixed or programmable band-pass filters. The sensed data can be processed in several manners, and each of these processes can be used to determine a specific characteristic of the stimulation signal. When sensed activity is evaluated for a tightly bound neuronal oscillation, the band-pass of the filter may be set to be relatively restricted (e.g. 0.5 Hz bandpass). The output signal, which may be based upon a filtered form of the input signal, may be generated utilizing an additional narrow-band filter to obtain measure which is an estimate of the frequency of peak spectral power, while a larger band-pass may provide a carrier signal which is more efficient in entraining a neuronal target. The peak frequency estimate can serve to create the envelope by which the carrier signal is modulated. The neural target may contain neurons with a range of natural frequencies that vary somewhat from the central tendency, causing periodic shifts in the peak frequency of spectral power (e.g., alpha rhythm) and consequently shifts in the modulation envelope of the stimulation signal. Alternatively, the stimulation signal may be a band-pass signal generated with or without sensed data. An arbitrary carrier waveform of specified spectral content can be created by using a random noise generator and then filtering this signal with filter settings selected in order to provide the desired carrier. The stimulation signal may be a selected band encompassing energy limited by a first frequency and a second frequency. In one example, the band-pass signal is chosen so that the band contains spectral content which lies primarily somewhere between at least approximately 0.5 Hz and at most approximately 20 Hz. The width and center frequency of the band can be periodically selected to provide measurement of a particular type of basal or evoked activity which is related to a symptom of the disorder. Although altering the signal characteristics of the stimulation signals based upon characteristics of the sensed data may be implemented in a manner that will cause the stimulation signal to alternate its characteristics over time, this does not occur in a strict manner. In other words, using characteristics of current sensed data to determine a stimulation signal will not necessarily be related to the characteristics of different symptoms such as their incidence, nor is it geared towards treatment of multiple symptoms of a disorder.

Roving Based Stimulation Strategies.

The device 10a can also provide therapy by stimulating at several therapeutic frequencies, rather than stimulating at a single particular frequency. For instance, stimulation can occur using a signal which comprises a consistently or periodically roving signal. The parameters of the signal may be defined to rove within a selected range, or across certain values, that have been found to produce therapeutic results. In one embodiment different values used in the roving therapy are related to the treatment of different symptoms of the disorder. Further, the roving may be adjusted so that it occurs according to the proportional incidence of different symptoms. In FIG. 7, step 200 can include creating a signal that roves over time. This signal is then subsequently applied during stimulation treatment 202. The method can also encompass periodically creating a new roving signal (returning arrow) and applying this 202. The steps of FIG. 7 can be done for one electrode contact, for all electrode contacts, and uniquely for all electrode conduits, and may include sequential activation of SEST-probes 31.

The roving of a parameter of stimulation protocol can be used to adjust the stimulation parameter values of a wide number of signals, such as the range, center frequency, rate of modulation, or depth of modulation, of: a frequency modulated carrier; a linear or logarithmic chirp waveform; dynamically adjusted band-pass noise, where the band-pass is changed over time. Roving may be used to adjust the parameter values of pulse type signals where a parameter such as duty-cycle is roved over time. The resulting stimulation signals therefore do not have a single frequency or rate of stimulation, but rather alternate between or rove across a range of therapeutic frequencies. These signals can have spectral and temporal profiles which are dynamic and temporally distributed. The signals may contain different spectral content at different moments of time, and energy from one or more spectral bands at particular moments in time.

The stimulation signal may be comprised of energy that spans across a range of therapeutic frequencies (e.g., it may rove between 1 and 18 Hz), and may contain spectral energy of which only a portion spans a therapeutic frequency range (e.g., 30% of the energy is between 1 and 18 Hz). All of these roving parameter values can be adjusted with respect the characteristics of one or more symptoms of features of the sensed data.

Roving signal protocols offer a number of additional advantages. For example, a particular frequency (e.g. 3 Hz) may not always be the optimum rate of stimulation. A particular spectral profile can serve to provide better therapy than others, due to such factors as changes in brain state. Such changes can be reflected by changes in the spectral content, or other measures of endogenous activity. When sensed data are not evaluated slowly roving the a parameter can still offer advantages over merely using a specific stimulation signal since it can modulate a greater assortment of neurons, during different brain states and in different manners. In the case of epilepsy, periodically or responsively alternating the spectral content using parameter values that have shown to produce good test results may deter a wider assortment of unwanted symptoms.

Roving the stimulation signal may also decrease the interference of stimulation with endogenous processes. For example, studies have shown that when low frequency stimulation, such as 3 Hz, is used in animals, that learning and attention may be impaired, while a repetition rate of 10 Hz or so does not lead to such impairment Oohn et al, 1961; Bawin et al 1973). Although many current stimulation methods use stimulation signals which are considerably faster, the incorporation of lower frequency signals should address this type of issue. The power and frequency of the alpha and theta rhythms have been shown to be related to perceptual framing, neural timing operations, and memory capacity and LTP (e.g., Huang & Kandel, 2005; Hwang et al, 2005; Varela et al, 1981) and stimulation which alters these rhythms on a long-lasting basis may result in disruption of the cognitive correlates. The magnitude of these side-effects may be subtle or moderate and can be measured by cognitive-behavioral testing or by neuroimaging/neurophysiological tests, including evoked potential testing, which may be used to guide the therapy program. In any case, chronic 3 Hz stimulation may cause memory, perception, or learning problems patients while a roving carrier can be used to minimize these unwanted effects. Additionally, while 10 Hz may be less effective in reducing or preventing the emergence of seizures than, for example, 3 Hz, it may work sufficiently well to act as a temporary substitute (as dictated by the roving protocol) so that 3 Hz stimulation does not continuously occur when it is interfering with endogenous brain processes. Since the two frequencies of stimulation may be able to block different types of seizures, roving the frequency of the stimulation signal would be better than using either signal alone. In other words the two parameter values defined for roving of the stimulation signal can be directed towards providing therapy to two different symptoms, which is a central advantage of the invention. When the function which guides the roving of a parameter value is discontinuous, the roving will be identical to alternating.

Selection of Roving Parameter Values and Multi-Protocol Treatment Programs.

The selection of two or more different stimulation parameter values may be done based upon sensed data obtained during therapy or prior to stimulation, during an initial evaluation period. The two or more stimulation signals can be chosen order to reduce the likelihood of two or more symptoms (e.g., in epilepsy treatment, two or more stimulation signals can be chosen order to reduce the likelihood of two or more seizure types developing in the brain).

In one illustrative embodiment, alternating between two rates (e.g., 3 and 5 Hz) is adjusted according to treatment of different symptoms. For example, a 3 Hz stimulation signal might be found to block 95% of seizures, while 4 Hz stimulation is found to block 1% of seizures, 5 Hz stimulation blocks 5% of seizures, and 6 Hz blocks 60% of seizures. If only one stimulation signal was to be used for basal stimulation then a 3 Hz stimulation signal would likely be selected. If two stimulation signals were chosen, these might be the 3 Hz and 6 Hz signals. However, the 5 Hz stimulation signal can prevent a different type of seizure than that blocked by 3 Hz and 6 Hz. Thus, alternating between 3 Hz and 5 Hz might be therapeutic than simply stimulating at 3 Hz, or 3 Hz and 6 Hz, since the two signals chosen provide therapy to two different symptoms of the disorder. Additionally, the stimulation signals can be provided in proportion to the incidence of seizures to which they are related. For example, if seizures blocked by 3 Hz occur 70% of the time, while seizures blocked by 5 Hz occur 30% of the time, then the stimulation signal may stimulate at either 3 or 5 Hz (or 140 and 180 Hz) for corresponding proportions of time or incidence (e.g., the method FIG. 8 using only steps 212 and 214).

If a first parameter value is useful for blocking a first category of seizure, and a second parameter value is more akin to blocking a second type of seizure, then determining the stimulation protocol using sensed data may occur using a number of strategies. A "historical strategy" may be particularly used when seizure prediction from sensed data is not very accurate. Historical strategies tailor the stimulation protocol based upon the number of past events which were detected over prior period. As is shown in FIG. 8, data are sensed 210 for a period which may be several days or weeks or longer, the sensed data are evaluated to measure the number of occurrences of one or more seizures over a selected period of time 212. The stimulation parameter values are then created for signals which are likely to block each seizure type 214, and these are then implemented by the roving stimulation protocol. The protocol can be designed based upon the proportion of different seizure types that were detected 216. This protocol is then used to provide stimulation 218. When prediction of seizures is more accurate, the number of responsive interventions for each seizure type, rather than seizures themselves, may be used.

Rather than stimulating with two types of signals, each of which is designed to treat a symptom, for example, desynchronize activity and prevent seizures, the different stimulation parameter values can be designed to treat a particular symptom in two manners. For instance a first stimulation protocol can use parameter values which have been found to modulate a particular level of neurotransmitter in regions which have been shown to decrease seizure emergence, while a second protocol can use parameter values which are found to block the emergence of activity which anticipates seizure emergence, for example, slow wave activity. The level of neurotransmitters in a region relevant to the symptoms of a disorder can be considered part of the brain's state. The selection and alternation of signals can be done (with or without sensed data) to maintain a brain state or neural state, by applying stimulation so that this state is controlled to remain within a normal range, a control range which may be user defined, outside of a critical range. The neural state is controlled to generally deter the likelihood of certain neurological signs or symptoms or precursors to these symptoms which may, for example, be abnormal patterns of activity (or patterns of coherence, synchrony, or disentrainment) related to EEG, neurochemistry, or bloodflow. Abnormal synchrony may be reflected in the sensed data by a number of measures. In the case of EEG, for example, coherence or synchrony measures may be obtained from two or more sensors, or a change in the spectral content obtained from one or more sensors, such as an increase in (or amalgamation of) power over a limited frequency range associated with a tremor or seizure symptom. Using non-linear measures, estimates of chaos, system-state, complexity, and other estimates may be used to provide measures of synchrony. The selection and alternation of signals can be done with sensed data to maintain or deter a brain state, neural state, symptom, or abnormal measure. The selection and implementation of parameters to accomplish this may occur using one or more algorithms or control laws which maintain a neural state or sensed parameter within a particular range with reference to reference state or value (e.g., U.S. Pat. Nos. 6,463,328; 6,366,813).

Further Considerations Concerning Endogenous Activity.

Commonly used therapeutic stimulation parameters for DBS (e.g., monopolar cathodic; 1 to 5 V stimulus amplitude; 60 to 200.mu.s stimulus pulse duration; 120 to 180 Hz stimulus frequency) have been derived primarily by trial and error. In some treatment applications, the parameters have been determined to be effective because of the nearly immediate effects of DBS for treatment of disorders such as movement disorders (e.g., tremor and Parkinsonian motor symptoms). The delay between initiating therapy with a set of stimulation parameters and the amelioration of symptoms, such as decrease of depression, may have a delayed time-course, as is often seen when treating these disorders with various pharmaceuticals. The successful stimulation parameters for the treatment of psychiatric diseases and more complex disorders can therefore be considerably more difficult to derive. Further, as discussed, there may be different mechanisms behind slightly different symptoms of a disorder, which require different treatments, and further considerable heterogeneity of symptom clusters which are uniformly classified as a particular disorder. Strategies which assist in selecting or applying stimulation which has an increased chance of being therapeutic, may become increasingly important for these more complex disorders. Successful treatment for a wide array of disorders may depend upon treating multiple symptom abnormalities, and will demand a more thoughtful consideration of the separate advantages of different types of stimulation methods.

Epilepsy may arise from the imbalance of excitatory and inhibitory processes. Enhancement of the activity of brain inhibitory mechanisms, mediated through chronic stimulation, has been shown to lead to a beneficial therapeutic effect for some intractable epilepsy patients. Since lower frequency endogenous potentials, e.g., 0.1 Hz to 10 Hz, are thought to reflect inhibitory processes, low frequency neurostimulation may increase inhibitory processes and decrease the emergence of seizures. Indeed, low frequency stimulation has been shown to provide anti-epileptogenic benefit (e.g., Velisek et al, 1986, D'Arcangelo et al, 2005; Misawa et al. 2005; Weiss et al, 1995). However, as noted, the picture is more complex since both low and high frequency chronic stimulation can decrease the occurrence of seizures. A model based upon an imbalance (generally up-regulation) of cortical excitability thus does not seem to be a simple story, since both low and high frequency stimulation can provide therapeutic benefit. In a pertinent illustrative example, Chkhenkeli et al, (2004), studied the inhibitory effects of chronic electrical stimulation in 150 patients with implanted intracerebral electrodes, with respect to neocortical and temporal lobe mesiobasal epileptic foci. Stimulation was provided to a number of structures including the head of the caudate nucleus (HCN), cerebellar dentate nucleus (CDN), and thalamic centromedian nucleus (CM). Results demonstrated that both 4-8 Hz HCN and 50-100 Hz CDN stimulation suppressed the subclinical epileptic discharges and reduced the frequency of generalized, complex partial, and secondary generalized seizures. Additionally, CM stimulation (20-130 Hz) desynchronized the EEG and suppressed partial motor seizures. It was also found that direct subthreshold 1-3 Hz stimulation of the epileptic focus could suppress rhythmic after-discharges. In this study, seizures were eliminated or greatly attenuated for 91% of the patients: chronic neurostimulation may generally suppress the activity of epileptic foci, and, in long run, stabilize the regions displaying epileptic foci activity. However, the spectral content of the signals that provided therapy varied greatly, in part as a function of location. Although direct brain stimulation, might serve as a useful tool in the treatment of intractable and multi-focal epilepsy, both low (e.g., 1 Hz) and high (e.g., 50 Hz) electrical stimulation have been shown to decrease or prevent seizures (e.g., Kinoshita et al, 2004). It is normally difficult to ascertain, even with extensive testing of the patient, which parameters may be most effective.

Roving between different stimulation parameter values is obviously one manner of addressing the treatment of different symptoms, or addressing the treatment of a particular symptom that may be treated in more than one manner (e.g. as can be varied due to changes in neural state which are only partially related to the disorder). However, when choosing parameter values which may be therapeutically beneficial, it is not always possible to determine how well various parameter values will serve to deter one or more symptoms. For example, a seizure may occur only once in several weeks or months and comparison between different stimulation signals in deterring the seizure may take years. Rather than evaluating how well different stimulation signals prevent or deter symptoms, stimulation parameters can be set or"prescribed" based upon the characteristics of endogenous rhythms of brain activity. These endogenous rhythms may, or may not, contain activity reflective of the events themselves. For example, peak frequency of beta power may be used rather than examining a characteristic of epileptiform activity itself. In one method of treatment, neurostimulation parameter values may be selected to create stimulation signals that match, mimic, or efficiently drive/disrupt, the endogenous rhythms of the neural targets. Rather than using arbitrary stimulation signals (e.g. 180 Hz pulse trains) which are largely above the frequencies of endogenous activity currently known to upregulate/downregulate activity when stimulation modulates neural tissue at slow rates, it may be adjusted as a function of these rates. A 10 Hz stimulation signal may be adjusted to 9 Hz if the patient's alpha rhythm shows a dominant peak at this lower frequency, since the brain is likely become more entrained as the stimulation pattern approximates (and drives) the brain at its naturally occurring rates. The stimulation parameter values which are selected may crate signals which are comprised of either low or high frequencies in different regions, and may be inhibitory, excitatory, synchronizing, or desynchronizing, in relation to the endogenous activity. Varying neurostimulation parameter values such as frequency, stimulation onset, or size of the stimulation signal, in relation to endogenously occurring EEG rhythms, in order to enhance or attenuate these rhythms, should improve the benefit of roving-based therapy, especially stimulation signals contain lower spectral power.

In contrast, regardless of the stimulation signal used, and the therapeutic benefit of either low or high frequency stimulation may be decreased and the emergence of unwanted and unpleasant side-effects may increased when the stimulation signals are too close to the normally occurring rhythms, due to interference with normal brain or cognitive functions. Therefore it may be better, in treatment of certain disorders, to avoid using stimulation parameter values that create signals which are too similar to endogenously occurring rhythms. The issue of unwanted side-effects related to cognitive interference, memory, and perceptual processes, has not been considered much by recent neurostimulation protocols. This issue may be highly relevant when using low frequency stimulation. For example, low frequency endogenous potentials have been shown to be intrinsic to both conditioning and higher order learning Oohn et al, 1961). Low frequency stimulation (or very high frequency stimulation pulses modulated at slow rates) which drives endogenous activity has been shown to both increase the development of conditioning to a stimulus, and decrease the subsequent extinction of the response during non-reinforced trials (Holt & Gray 1985; Bawin, et al, 1973). Alternatively, low frequency stimulation which occurs at different frequencies than those which occur endogenously, or which disrupts the endogenous low frequency rhythms, has been shown to have little effect, or to slightly impede learning. John et al (1961) examined using low frequency stimulation by using a 100 cycles per second (CPS) biphasic pulse carrier, which was modulated at low rates of either 4 or 10 CPS, and found that the 4 Hz modulation was much more inhibitory than 10 CPS and led to decreased conditioning in some animals. Accordingly, while chronic or semi-periodic stimulation of various brain regions can be used to decrease the presence of unwanted activity such as seizures, it may also cause unwanted side-effects such as interference in attention or learning. By roving the neurostimulation parameters so that the stimulation frequency is not held constant, the effects of this neurostimulation on factors such as learning and attention may be decreased, while the therapeutic efficacy of the stimulation persists.

Additionally, studies have shown that neurostimulation is able to increase the intrinsic firing of low frequency endogenous potentials, when the neurostimulation frequency is matched with the internal frequency, while when the neuro stimulation frequency is different from the internal frequency in a similar range, the neurostimulation may act to block this activity or lead to an augmentation of activity in a different frequency range (which may not be within the same frequency range as the neurostimulation signal). In one embodiment, endogenous brain activity can be reinforced by neurostimulation using a method where data are sensed from a sensor, and the sensed data are processed (e.g., amplified) and becomes a signal which sent to a filter, the filter having a band-pass that has a center frequency which is intended as the neurostimulation frequency, and wherein the output of the filter is used as a neurostimulation signal at one or more leads. The center frequency of the filter can be determined by the dominant peak frequency of the endogenously occurring activity, and the neurostimulation can be triggered when the output of the filter is above or below a specified level, or can be provided responsively based upon a different strategy. Accordingly, if synchronized activity was sensed from a target region, this signal could be used to create a stimulation signal that could be fed back to one or more stimulation electrodes either in phase, out of phase, or with a specific time delay (each of which may be individually set for each electrode contact) in order to reinforce, disrupt, or adjust the endogenous activity. Further, since the dominant frequencies of the internal rhythms can reflect the envelope of the population activity, and the likelihood that a cell will fire is somewhat dependent upon the pharmacological and electrical characteristics of the extracellular space, the electrical stimulation can have differential effects when introduced at different states of the internal rhythm. In other words, the same signal can have different effects when introduced in different neurophysiological "states". The stimulation signals can be adjusted to occur at different lags in relation to the endogenous activity in order to increase the influence of stimulation.

The stimulation signal that is applied can have a spectral/temporal content which is set (to be a different from the endogenous frequency) in order to entrain the population at a spectral frequency that is not related to unwanted symptoms of a disorder This method could be used to treat disorders such as pain, tremor, epilepsy (seizures), depression, or other disorders where behavioral symptoms are associated with an increase in synchronized firing of a brain region in a particular frequency. In the first step, a band-pass of the filter can be programmed using bands relied upon by conventional quantitative-EEG. If a signal with a peak frequency between 4 and 8 Hz is desired then the center frequency of the band-pass can be determined by, or set to measure, the peak frequency in the EEG in that range (theta range), while a roughly 10 Hz stimulation signal is desired then the center frequency of the band-pass can be determined by, or set to measure, the peak frequency in the 8 to 12 Hz range (alpha frequency). The dominant frequency of the stimulation signal can be set to be 1 or 2 Hz above the peak frequency detected within the selected band. In other words, by driving the brain at a frequency which is one or two Hz away from the dominant frequency of a tremor, the tremor may be attenuated.

When the neurostimulation signal is modulated at, or promotes entrainment at, frequencies which are different than the endogenous EEG patterns, the neurostimulation will attenuate the endogenous activity and promote activity at other frequencies, even though these may be different than the stimulation frequency (Bawin et al, 1973). While the issue, of matching endogenous brain activity in order to enhance entrainment and modulation effects, should be addressed when providing therapy for a wide array of disorders, this may be especially important for brain stimulation. While only certain portions of the brain follow frequencies above 80 Hz, both cortical and sub-cortical structures naturally produce rhythms at these rates, such as the conventional QEEG rhythms which are approximately, delta (0-4 Hz), theta (4-8 Hz), alpha (8-12 Hz), beta (12-18 Hz) rhythms and the famous 40-70 Hz gamma-band response which is related to binding of multi-modal stimulus features, and the formation of percepts. Alternatively, other the EEG can be evaluated using different bands of spectral energy. Additionally, event-related components such as the N100, P300, N400 and numerous well known components have spectral components between 1 and 200 Hz, and stimulation of structures involved in these responses at frequencies which they use functionally, may cause disruptions in brain processes, such as those related to sensory evaluation.

Methods and systems for improving treatment by incorporating measures of the sensed endogenous rhythms of the brain or body can be relatively simply adapted (e.g. FIG. 11). A filter can be used having a band-pass (for example, the 4-8 Hz range) which allows the activity of a specific structure, such as the hippocampus, to be sensed. This data is then used in the generation of the stimulation signal in order to be supplied with a specified relation (e.g. match or avoid) to the sensed endogenous activity. Additionally, an envelope based upon a band-pass endogenous EEG signal can be applied with a phase which either positively or negatively reinforces the endogenous activity 126, or which occurs with a specified relationship (i.e. phase, time, relative frequency difference) to this activity.

Several methods may be used to positively or negatively reinforce endogenous activity or to achieve a different advantage. In the method shown in FIG. 10, the treatment program 300 selects one or more stimulation signals 110, from the database 20 of the implantable system 10a. In the next step data are sensed 112 and the sensed data are processed in order to obtain a measure of a relevant characteristic 114 of the sensed data. Examples of relevant characteristics are: phase of a specific frequency; the peak frequency of a frequency band; the spectral profile of a portion of epileptiform activity; and, the relative power of a frequency band compared to a reference band of activity, which may be the same band at a different time. Neurostimulation is then provided whereby the stimulation signals are adjusted according to this measure so that these positively or negatively reinforce endogenous activity 116. In other words, the relevant characteristic can be the phase of an endogenous rhythm, and the neurostimulation signal can be provided with a time delay to be either approximately in-phase or out-of-phase with the endogenous signal. In addition to matching or avoiding matching the spectral composition of the endogenous activity, the amplitude of a sensed signal can be related to the amplitude of stimulation signal. This would be useful in the case where larger tremor activity results in a neurostimulation signal of larger amplitude. Step 116 may entail using stimulation signals which are selected and subsequently modified by the stimulation subsystem 14, according to one or more measures of the relevant characteristics in order to provide signals which are inhibitory or excitatory with respect to the endogenous activity.

Yet another alternative method is shown in FIG. 11. Rather than using pre-defined stimulation signals, as in FIG. 10 data can be sensed 120, and this sensed data can be processed 122 to select or create the stimulation signals based upon one or more measures of the relevant characteristics of the data 124, prior to stimulation occurring to positively or negatively reinforce endogenous activity 126. In one embodiment, the sensed data can be obtained 120 and then processed 122 by filtering it from 4-8 Hz to determine the endogenous theta activity of the subject, and the stimulation signal is then created based upon the relevant characteristics such as the peak frequency and phase of the filtered signal 124. This stimulation signal is then applied to reinforce endogenous rhythms, either positively or negatively 126, and applied relative to the phase of the endogenous rhythm. The envelope of the power of the filtered activity can be used to modulate a carrier signal that entrains neural activity better than the endogenous spectral constant, in order to synchronize or desynchronize activity neural targets. In any case, the stimulation signal derived from sensing the endogenous signal can be stored and subsequently presented with independent delay, at different electrodes. This method can be used to synchronize or desynchronize neural activity related to disorders which manifest abnormalities of synchronization, such as tremor, epilepsy, or depression. Another method is to create the stimulation signal itself from features of the sensed data, such as can occur by narrow-band filtering the EEG to obtain the envelope of activity related to a particular structure, and then presenting this envelope as a signal having an amplitude which is adjusted in relation to the endogenous signal. A proportional-amplitude frequency-matching control law circuit is another manner of accomplishing this type of signal. A proportional-amplitude frequency-matching control law circuit is another manner of accomplishing this type of signal In one embodiment of the method which utilizes endogenous rhythms in creating the stimulation protocol, the stimulation signal is chosen to have a frequency which is slightly above, or slightly below the spectral frequency of the endogenous signal, for example, in order to entrain the natural rhythm at faster or slower rate, respectively. In another embodiment, the stimulation signal is chosen to have a frequency which is considerably above, or below, the spectral frequency of the endogenous signal, for example, in order to decrease the risk that the stimulation interferes with the endogenous activity. The frequency difference between the endogenous rhythm(s) and the stimulation signal can be determined empirically in an automatic or semi-automatic manner, where the separation is iteratively increased until the desired results occur. The frequency difference can also be an absolute value such as increasing the stimulation frequency by 2 Hz relative to the sensed oscillation, or can be a percentage such as increasing the stimulation frequency by 10%, relative to the average frequency of the endogenous rhythm. In another embodiment, in steps 122, 124, and 126, the filtered signal is amplified and used as the stimulation signal provide concurrently or subsequent to the sensing operation.

Additional Spectral Considerations and Embodiments

When selecting parameters for a stimulation signal, such as an amplitude-modulated carrier signal, the spectral characteristics of the carrier are as important as the modulation rate. For example a carrier signal of 200 Hz which is amplitude modulated at 3 Hz, has a spectral energy in a very different band than when a carrier of 100 Hz is used. The power spectrum of an amplitude modulated sinusoid signal will show energy at the carrier (i.e. 200 Hz) and at 2 side-bands which are separated from the carrier by the frequency of modulation (197 Hz and 203 Hz). This signal will not have any energy at 3 Hz. However, the neurons in the brain will act as non-linear rectifiers that increase their firing during each rise of the envelope of the modulated signal. Accordingly, neural activity will be entrained at the modulation rate, although no energy occurs in the original signal at this rate.

When the spectral energy of the carrier is increased, for example, to values above 0.5, 2, or 4 kHz, a threshold will be found which is above the low-pass characteristics of the a cells firing capability (e.g., due to upper limit of firing). The modulation rate of this signal may become the functional stimulation rate in this instance. The spectral content of high-frequency carriers will affect the ability of the signal to entrain neurons at the modulation rate and for transmission of the signal through tissue. The use of modulated carrier signals, where the carriers have spectral frequencies far above 100 Hz may be more beneficial in some applications. For example, in some individuals, 100 Hz energy may lead to seizure initiation rather than inhibition, and using energy far beyond this frequency range is preferable. Rather than using an amplitude-modulated carrier, a high-frequency carrier-signal could be mathematically combined with a lower frequency stimulation signal, and would ride on top of it (i.e. the stimulation signal can be added to the carrier rather than multiplied with it). In this embodiment, the modulation signal would preferably be in the range of 70% to 90% of the energy and the supplementary (high-frequency) signal would be on the order of 30% to 10%. In other words, for example, a primary signal of sine wave from 0.1 Hz to 20 Hz with secondary signal consisting of, for example, a noise signal or a second sinusoid is superimposed. This superimposition can be done to increase the efficacy of the stimulation, energy transmission and reduce the risk of tolerance, where the secondary signal is about 20% the magnitude of the primary signal.

In addition to the embodiments described, the neurostimulation signal could comprise a modulated carrier, where the modulation rates are between approximately 0.1 Hz and 20 Hz, and the amplitude-modulated carrier signals are periodically or continuously varied in their spectral profile. One reason for this variation would be to increase signal transmission through tissue or decrease habituation and tolerance. A sinusoidal waveform that has higher frequencies, such as harmonics, to assist in recruiting the neural response may also be used. In a general embodiment, the method includes selecting or adjusting the first stimulation signal which is preferably a signal is a non-pulsitile waveform, (e.g., a sinousoid), which has been selected in order to provide treatment, and then combining this with a second signal which is superimposed in order to provide a secondary advantage such as a better transmission from electrode to the tissue or through the tissue itself, better entrainment of a tissue target, reduction of an unwanted side-effect, or differential stimulation of a particular subset of neurons. Amplitude modulation does not have to occur with a depth of modulation of 100%, and the depth of AM can be a parameter of the stimulus protocol which can be set or roved.

Generally then, these principals can be embodied in the following preferred method. The first step of the method a first stimulation signal is selected and adjusted to provide therapeutic benefit. In the second step of the method, a second stimulation signal is combined with the first signal, and iteratively adjusted, in order to provide an additional advantage. The additional advantage can be decreased side-effects, increased transmission, etc. When 2 or more stimulation conduits are close enough for their fields to interact, the two signals can be supplied by these conduits (although this will only provide for addition of the two signals and not multiplication). If the first and second signals are combined by multiplication then the complex waveform will often resemble an amplitude modulated waveform, especially when the amplitude of the first and second signals are similar. If the first and second signal are combined by addition, then the combined signal will often approximate a signal which looks like the perturbation of one signal by the other, especially when the first and second signal different in magnitude by a factor of 2 or more. When the stimuli are non-pulsatile carrier frequencies, is contemplated that the spectral content of first signal will normally be different from the spectral content of the second signal by a factor of at least 2 and the amplitudes will differ by a factor of at least 3.

This use of higher frequency addition to a relatively slow frequency carrier is important in order to improve the ability of the signal to stimulate the intended region. In fact, small changes in spectral characteristics of arbitrary signals as well as pulse-trains can have significant effects in terms of providing therapeutic benefit of neurostimulation. The electric fields generated by the neurostimulation leads are dependent on both the shape of the electrode and also on the electrical conductivity of the tissue. In the central nervous system conductivity is both inhomogeneous (dependent on location and the type of cells in that location) and anisotropic (dependent on direction or orientation of the cells with respect to the stimulation field). The inhomogeneity and anisotropy of the tissue around the neurostimulation electrodes can alter the shape of the electric field and the subsequent neural response to stimulation. The result of the neurostimulation is complicated further by the effects that the fields will have on the individual neurons. The second derivative of the extracellular potentials along each process will invoke both transmembrane and axial currents that will be distributed throughout the neuron (as can be computed from the cable equation). In turn, each neuron exposed to the applied field will be affected by both inward and outward transmembrane currents and regions of depolarization and hyperpolarization. These types of complex responses to stimulation have been examined and verified in a large number of experimental preparations demonstrating the differences between anodic, cathodic, and bipolar stimulation with respect to activating and blocking neural activity using extracellular stimulation (Mclntyre & Grill, 2002).

Likewise, by slightly modulating a slow wave stimulation signal using a higher frequency perturbation, the effects, due to the variations in the generated fields (including their functionally relevant shapes), will be different. These variations can effect energy transmission and entrainment and/or can specifically affect certain neurons in order to compensate for the limited resources available when working with implanted systems which rely upon fields that are generated from neurostimulation electrodes of fixed locations.

One embodiment which can be used with either electrical or magnetic stimulation utilizes a modulated carrier with a center frequency of between approximately 200 and 1000 Hz. And another embodiment, uses a carrier with a center frequency of between approximately 1 and 100 kHz. A band-pass noise stimulus can be used having energy between approximately 0.5 and 20 Hz. The term "energy between approximately 0.5 and 20 Hz" may be understood, in some embodiments, as a band of energy which may span 1 Hz or more. For example, the band of energy may span approximately 4 Hz and be centered at 6 Hz, with slightly more energy at the 2 higher frequencies of the band.

While prior art, such as the '770 application, describes using low frequency stimulation, the signals described here are not anticipated from the prior art. The '770 a dual-stimulation strategy incorporating a non-responsive "low frequency stimulation having a primary frequency of around 0.5 to 15.0 hertz" in the treatment of disorders such as epilepsy, unlike the current invention, it does not describe using amplitude modulated carrier signals having rectified energy primarily between approximately 0.1 Hz and 20 Hz and also does not describe using amplitude-modulated carriers where the modulation frequencies are between 0.1 Hz and 20 Hz, and in which the spectral content of the carrier signal is varied in order to improve therapy (e.g., increase signal transmission through tissue, increase entrainment of neural tissue, or decrease habituation and/or tolerance). The methods described here include embodiments where sensed data is used to create the stimulation signal and, based upon the band-pass of the amplifier, the resulting stimulation signal contains spectral content between 0.1 Hz and 20 Hz. The inventive methods also may be realized using control laws and control circuits where the parameters which guide the control processes, or the processing of the signals sent to or from the control processes, are set or adjusted in order to produce methods or signals a described herein. It is understood that stimulation strategies which utilize sensed data, with or without control laws, may be adjusted and designed to incidentally, periodically, and even responsively, provide stimulation with the signals and strategies described herein, and such implementation is understood to be part of the claimed current invention.

The invention provides methods and systems for improving treatment by providing a stimulation signal which sweeps or alternates a stimulation parameter such as the repetition rate, the instantaneous spectral content of the stimulation signal, or the center-frequency of a band-pass signal, using values for the parameter which have been shown to provide desired therapy during a selection procedure. Carrier signals which are modulated to provide a rectified signal with spectral energy between approximately 0.1 Hz and approximately 20 Hz, are a preferred embodiment, although for applications related to, for example, cortical stimulation, modulation may occur using stimulation signals with alternative spectral signatures, for example, those of the gamma range (i.e., 40-100 Hz). The carriers can be selected based on their ability to entrain target tissue. A band-pass filter can be used to filter endogenous EEG activity, sensed from a sensor, in order to generate one or more low frequency stimulation signals which are in-phase with, and which drive, the endogenous signals of different brain structures (e.g., the thalamus, basal ganglia, amygdale, or hippocampus) or which has some other phase relationship to the naturally occurring signal.

In another embodiment, the stimulation signal is comprised of a modulated noise carrier. If the noise is low passed, the resulting stimulation signal will approximate a sinusoid with random fluctuations. Accordingly, the signal may never repeat since no two segments of the signal will be the same, unless of course the signal is stored in a circular buffer, in which case the repetition rate will be the inverse of length of the buffer. The different shapes which are produced by the random fluctuations of this signal may be advantageous, over using an unchanging stimulation signal, since these have a greater probability of stimulating various types of neurons within the target tissue, and may be less prone to certain types of habituation or adaptation. Further, the transfer of energy through the neural tissue may be somewhat dependent upon the shape of the stimulation signal, and may also affect the ability of a stimulation signal to stimulate different neurons.

Further, rather than using a stimulation signal that oscillates, one can use a slowly alternating DC stimulation (this may approximate a square wave signal), where the signal stays at some positive voltage value for a given amount of time and then switches to a negative value after a 1 or 2 second period (or when a seizure is predicted to occur in the near future). As in the case of the 3 Hz stimulation, a simple occasional switch in polarity may cause the extra-cellular environment to be destabilized to the point that seizures cannot be generated, but the inhibitory effect of slow wave stimulation on learning and other cognitive processes can be avoided.

A method of treating a disorder comprising alternating the treatment protocols between 2 or more candidate treatment protocols (or parameter values), wherein a first candidate protocol provides a first therapeutic benefit and a second candidate protocol provides a second therapeutic benefit, and said first and second therapeutic benefits are at least partially independent and may be related to treating two types of events related to the disorder. The two protocols can be provided in an overlapping, interleaved, alternating, or roving fashion. The protocols can provide stimulation according to signals which are supplied to the same stimulation conduit, different conduits, or different conduits which are close enough that their fields interact.

The method of treating a disorder in which the stimulation occurs with a stimulation signal comprised of at least two components, wherein each component is directed towards a different symptom of the disorder.

The method of treating a disorder comprises providing a stimulation signal with at least two components, wherein the first component is therapeutic but also causes an unwanted side effect and the second component is provided, selected, or adjusted to decrease the unwanted side-effect. The side-effect could be stimulating a neural target indiscriminately, and the second component causes an increase in the selectivity of the stimulation or the side effect could be the inadvertent disruption, enhancement, or entrainment of a particular endogenous rhythm and the second component can be a reduction in this inadvertent effect.

The method of treating a disorder comprises providing a stimulation signal with at least two components, wherein the first component is therapeutic and where the second component is provided, selected, or adjusted to make an improvement of the first component. The improvement could be stimulating a neural target more specifically, decreasing the disruption, enhancement, or entrainment of a particular endogenous rhythm which is not related to the treatment benefit, enabling better transmission of the first component with less power, decreasing impedance at the electrode-tissue junction.

Changing the Fc while maintaining a constant modulation rate may increase energy transmission or entrainment of a neural target. One embodiment of the invention describes methods to permit increased stimulation efficacy, by tailoring the Fc and Mf characteristics to increase transmission of the stimulation signal. Changing these characteristics can also improve therapy by decreasing the chance of habituation or adaptation by the tissue. The carrier frequency (Fc), or the modulating contour or its frequency (Fm) can be adjusted at specified or random intervals, or according to sensed data. Sensed data may be used to provide the modulation envelope for a carrier signal, or the timing of a pulse signal, in applications where sensed data is fed back to the brain in a closed loop fashion to promote or deter that activity. This method is an advantage when the modulated carrier, or windowed pulse train or pulse signal, is more efficacious in entraining tissue than stimulation which simply provides the modulation envelope itself.

The two signals can be generated by two different control laws, or control circuits, and provided as the stimulation signal at one lead. These methods can be accomplished wherein, the two or more components of the stimulation signal can be generated by two or more different control laws, or control circuits, and provided as the stimulation signal at one lead.

The present invention can assist in entraining endogenous signals via neurostimulation. In one alternative embodiment shown in FIG. 11, neurostimulation occurs using a stimulation signal that is based upon the output of a band-pass filter that filters endogenous EEG activity that is sensed from a sensor. The band-pass may be set to pass only low frequency (e.g., 4 to 8 Hz) EEG which can be used to generate a low frequency stimulation signal which is in-phase with the endogenously generated signals (for example, the signals generated structures such as the thalamus, basal ganglia, amygdale, or hippocampus). One rationale for this approach is that it may decrease the risk that the stimulation interferes or attenuates the naturally occurring rhythms of the brain. In this manner the neurostimulation acts to drive or enhance endogenous signals rather than occurring arbitrarily. In this example, the stimulation signal does not have a specific and definable frequency of stimulation since the waveform would rove in its frequency (and possibly amplitude) characteristics based upon fluctuations in brain activity. However, it would often be primarily comprised of approximately 4-8 Hz activity, if the sensed signal was coming from a sensor which sensed activity of a brain generator which produced oscillations in this frequency range, such as the hippocampus.

Methods for Selecting and Evaluating Treatment Protocols.

A number of methods are needed to increase the chance for providing and maintaining successful therapy during treatment. Even if the parameters of a default stimulation protocol are initially well chosen, over time, the stimulation signal may loose its therapeutic efficacy. In this case, therapy should be altered in an attempt to reestablish benefit. Several methods can be used in order to evaluate how well alternative stimulation parameters (including those of the partial signals) may serve to provide therapy compared to the baseline condition (i.e. the current default protocol). The methods generally adjust at least one parameter of the treatment protocol, and may be invoked if sensed data indicates that treatment benefit has decreased below a specified criterion. These methods can also be invoked periodically, for example, to simply explore if other parameters can provide advantages in the provision of therapy. Methods are described which automatically, or semi-automatically, under user guidance may be used to select appropriate values for the parameters of the treatment program, most routinely to create the signals used in the stimulation protocol.

In one embodiment, shown in FIG. 12, a method is illustrated wherein the value of a treatment parameter is varied one or more times and sensed data are collected and processed in order to determine if one or more alternative values can successfully provide improved treatment. This method can be applied to many disorders, but is illustrated in the treatment of epilepsy. In FIG. 12, the method is used for evaluating epilepsy treatment protocol parameters and accordingly the test score which is evaluated is a seizure score. However, it is obvious that in different disorders this test score can be related to symptoms of those particular disorders, and can be, for instance, test scores related to tremor size, duration, and location, or to neurotransmitter levels, and can be multivariate test scores related to data sensed by multiple sensors.

Parameters can be compared by creating a histogram of the number of seizures which occurred during each of the values tested for the stimulation parameter, with the bin-width being equal to the step size of the tested parameter or bin-width being amalgamated over a specified range. One or more stimulation parameters can then be selected and used during treatment based upon the seizure test score for the parameters, where parameters which meet a criterion value (produced the lowest scores) are chosen. In one embodiment of the present invention, the stimulation frequency is iteratively swept from approximately 0.5 Hz to approximately 20 Hz, in 1 Hz steps or at rate of 1 Hz per N minutes, and the seizure test scores during each frequency of stimulation are calculated. Alternatively, after a treatment with each frequency of stimulation a probe stimulus is applied at or near the stimulated region and an evoked response (e.g. epileptiform activity) is collected. The frequencies of stimulation which produced a desired characteristic in the response (e.g., the smallest amplitude or shortest duration evoked response either of which may be representative of decreased reactivity) can be selected to be used during the subsequent treatment.

In step 130 neurostimulation is provided according to a protocol, which may be a preferred protocol which has previously been selected, and which provides a particular stimulation signal to at least one SEST-probe 31. In step 132 baseline data are obtained and are then processed in order to obtain a baseline seizure score 134.

The processing of the data 134 can lead to one or more baseline scores. A score can be a single multivariate score which can be based upon the number, size, and type of seizures which occurred. For example, the score can be computed from a weighted multivariate equation which combines number, size and type using an equation $4N_L + 2N_S + 4(T)$ where NL is the number of large seizures (which may be defined as having a magnitude or duration which surpasses a specified criterion), NL is the number of smaller seizures (that are below the specified criterion), and T is the type of seizure. "T" may be assigned a number based upon the position where the seizure activity originated (e.g., which electrodes detected its emergence first) and the number related to its relevance to the disorder, or the number can be based upon other characteristics which are deemed to be related to seizure type or severity. Additionally, more than one score can be computed wherein each score is related to a different symptom of the disorder. This latter type of test score can be termed a "symptom score". When done over two or more testing periods, each test score can include statistics related to the score such as mean and standard deviation.

In step 136 one or more parameter values of the protocol are changed. Parameter values can be, for example, the duration or magnitude of stimulation, or the time between stimulation periods, and stimulation again occurs 137 with parameter value(s) set to the new value(s). Test data are then sensed 138 to permit the evaluation of the effects of this change. In step 140 the test data are evaluated to provide one or more test scores and in step 142 the at least one baseline seizure score and at least one test seizure score are compared to obtain a test result. The comparison operation may utilize one or more statistical criteria in order to ensure the test result occurred for at least a specified probability level. The test result may be binary, being "positive" or "negative", or may be quantified. If the test result is negative then there is no difference between the baseline and test seizure score. If positive, then a change has occurred and the test result may also have a sign value associated with it representing the direction of the change. The difference between the two scores may have to reach a criterion, which may be a statistical criterion or simply a threshold which is related to the size of the difference in order for a positive result to occur.

In step 144, the test results are evaluated and a treatment parameter is altered, or not altered, as may occur according to an algorithm implemented by a therapy program 300. As stated, the test result which is passed from step 142 on to step 144, may be binary, may have a statistical significance value attached to it, and can also have a quantitative aspect, such as the size and direction of the difference between the two scores or the scores themselves.

In one embodiment, in step 144, the treatment program dictates that if no improvement was found, comparison to the of the test seizure score to the baseline score produces a negative result, the value of the parameter value is changed (e.g., increased), and step 137 is repeated (arrow). A positive result causes step 146 to occur (although this may be made contingent upon the direction of the change). In an alternative embodiment, the test result is ignored, and the value is changed before repeating step 137, this can occur in order to provide two or more test results prior to causing step 146 to occur.

In step 146, the program is terminated and one or two other actions may also occur. In one embodiment, a value which produced an improvement of the test score relative to the baseline score is used to set the parameter value of the protocol that was being tested, and this is then used to provide subsequent therapy. In an alternative embodiment, when several test scores were obtained, an algorithm evaluates the scores and selects one or more values that resulted in positive test scores. For example, the test scores can be ranked and the values associated with the top (or bottom) 3 scores can be selected for use in the treatment program. Additionally, the scores may be symptom-scores which are related to two or more distinct types of events, and the meta-analysis program selects the values which produced the highest scores for two or more symptoms scores. These values can then be used by roving methods to deter the two different symptoms when roving or alternating stimulation signals are implemented.

In one very useful alternative embodiment, the parameter which is changed is the time between stimulation periods, and in step 144 the inter-stimulation period is iteratively increased until an a positive test result is obtained. In step 146, the meta-analysis algorithm may then cause the inter-stimulation period to be decreased by a specified amount such as decreasing the interval to the last inter-stimulation period which did not produce this change in test seizure score compared to the baseline seizure score. When "inter-stimulation period" is the parameter that is investigated using this method, then this will lead to less than continuous stimulation while still providing similar deterrence of seizures, and will utilize less energy, and potentially cause less side-effects and be less prone to habituation. This method can be used so that advantageous inter-stimulation intervals can be determined to treat various disorders. Generally, stimulation occurs by periodically applying non-responsive or basal stimulation, and increasing the duration between consecutive periods of stimulation until the number of the unwanted events increases (as may be determined by analysis of sensed data indicating a score which doesn't meet a criterion), and then decreasing the inter-stimulus duration below this amount. By using this technique power is saved while efficacy of treatment is maintained above a specified level.

A subset of the steps of this method can be adopted in order to provide additional routines useful in evaluation of stimulation treatment. Step 130 can be omitted in order to compare the values used in the test stimulation to a non-stimulation baseline state. Additionally, a different set of parameter values can be relied upon in order to simply evaluate different values of the treatment protocol from time to time. For example, by performing steps 137, 138, and 140, two or more times (i.e. stimulate, sense, process to obtain test scores) and then performing the meta-analyses of step 146 one or more preferred values can be selected to be used in the treatment protocol. By only including steps 137 to 146, and using a reference value other than the baseline score, the test scores can be compared to a user defined criterion (i.e., the reference value). In the case when the test result is either "positive" or "negative", these terms will obviously be relative to the criterion being used. A score of 3 would fail if the criterion was >5 and pass if it was <5, but in a preferred embodiment, the terms "positive" signifies that a test score has successfully met a threshold set by the treatment criterion.

Conversely, rather than being omitted, steps can be repeated. Further, if steps 130, 132 and 134 occur multiple times, several scores can be obtained and statistics can be computed on these to determine if any differences are "real" with respect to the variance of the test scores obtained with different parameter values. Statistical estimates can be useful in order to enable subsequent statistical comparison of the baseline scores to test scores, in order to avoid changing the protocol according to results that occurred by chance or were unreliable. Obviously steps 136, 138 and 140 can be repeatedly done as well to provide statistical estimates for the test-result data. Additionally, although step 132 occurs after step 130 in the diagram, the baseline data can be sensed approximately at the same time that the neurostimulation occurs, for example, in periods after one or more intervals of neurostimulation, and sensing can occur in an interleaved fashion with the provision of neurostimulation according to the protocol.

The method shown in FIG. 12 can be accomplished periodically to ensure that stimulation parameters are effective and advantageous for example, once a week or once a month. If there are diurnal related changes in a disorder, this method can be accomplished more than once a day and, for example, evening and morning protocols can be established separately. The method may be applied to any aspect of the treatment protocol, and not only to the stimulation protocol. Notably, when sensed data are used to create the stimulation signal, as may occur using control laws, the method can be applied to adjust the values related these laws. Rather than sensed data being evaluated automatically, it is likely that the test results will often be provided to the patient programmer 500 so that these can be evaluated by a user, who will then select successful candidate values. In addition to sensed data obtained from implanted sensors, test scores can be related to behavioral, cognitive, or emotional measures indicated by the patient using the programmer 500. In addition to parameter values related to the stimulation signal, different roving parameters relating to the rate of roving can be assessed using this method.

An alternative method evaluates two or more values of a parameter during the testing period, rather than testing these in discrete iterations as generally occurs in the method of FIG. 12. Over a specified time period a parameter such as the frequency content of the neurostimulation signal can be iteratively roved or alternated with potential parameter values and the effects can be assessed so that advantageous parameters are selected for use in treatment. FIG. 13 demonstrates an embodiment of such a method wherein a step 150 comprises applying neurostimulation according to Protocol 1, which uses a strategy such as roving or alternating to test values related to specific parameter. For example, the frequency is roved across a specified frequency range (e.g., either carrier frequencies or modulation frequencies are iteratively varied). In step 152, the test data are subsequently sensed after each new iteration, or after the data from several iterations have been averaged, and then the test data are processed to determine the seizure scores associated with each value of the tested parameter 154. One or more stimulation parameter values can then be selected by the meta-analysis algorithm and used during treatment based upon the seizure score for the parameters. In one obvious embodiment, the parameters which produced the lowest scores are chosen 156 and used to create protocol 2158. In one embodiment of the present invention, the stimulation frequency is iteratively swept and the number of seizures which occur during each frequency of stimulation are recorded, and at least 2 or more parameter values which resulted in the least number of seizures during the testing period are then selected to be used in during the subsequent treatment with Protocol 2160. In another embodiment, only 1 parameter is chosen based upon a comparison of seizure scores.

The method may only include steps 150 trough 160, in order to select values for the stimulation parameters and provide treatment, or may also include steps 162-164 to provide a secondary component of the method which allows for adjustment of Protocol 2. In step 162, treatment data are sensed and evaluated to determine if treatment meets a specified treatment criterion selected by the treatment protocol. This comparison produces a test result that, again, can be binary, quantitative (with sign indicating direction of change), and/or statistical. In step 164 three different results may occur which are illustrated by three different paths. Path 162a is followed when a treatment criterion is met, which simply returns the method to step 160, so that stimulation again occurs using the current protocol. When treatment criterion fails to be met, step 164 can follow paths 164b or 164c. Path 164b causes the method to be restarted from scratch and new values are obtained for the parameter. Path 164c causes step 166, in which adjustment occurs as is defined in the treatment program 300 (e.g. use a past successful parameter value). Step 166 can also be utilized when treatment criteria are almost met and a relatively minor adjustment (e.g., increasing voltage slightly) may again cause the criteria to be met. The situations in which 164a, 164b, and 164c occur can be dictated by a treatment evaluation algorithm used in the treatment protocol during step 164. In this manner, the type or magnitude of treatment failure can be evaluated and can result in either changing the stimulation protocol slightly in order to attempt to produce treatment success or can require stimulation parameters to be re-evaluated in a more comprehensive manner. One criterion for returning to step 150, can be defined as continued negative test results having occurred a specified number of times using step 166 within a specified time period. FIG. 13. also demonstrates a method of adjusting a the protocol, a little or a lot, based upon comparison of treatment response to treatment criterion, and whether the comparison failed by a little, or a lot. In other words, the size of the test result can determine subsequent operations of the method.

Transcranial Magnetic Stimulation Applications.

US 20030028072 entitled 'Low frequency magnetic neurostimulator for the treatment of neurological disorders' (the '072 application) describes a system for treating neurological conditions by using low frequency time-varying magnetic stimulation. The application describes applying energy in a range below approximately 10 Hz to the patient's brain tissue and also describes an implantable embodiment where direct electrical stimulation is used. The '072 application describes using a carrier waveform of about 100 Hz which is pulsed at different rates. Unlike the '072 application the current application describes matching, adjusting, or avoiding matching the rate or pattern of stimulation to, or in relation to, endogenous rhythms in the brain (especially those below about 18 Hz) in order to increase the efficacy of treatment. By adjusting the modulation or pulsing of the stimulation fields so that these match or resonant with the internal rhythms of the brain, the slow frequency rhythms (or slow frequency amplitude modulation of high frequency pulse stimuli) can be augmented (Bawin et al, 1973) or inhibited. Magnetic stimulation using two or with more coils whose signals produce a vector field having spectral characteristics which are different than the constituent signals can be implemented by the systems of the '072 application.

Figure 15:
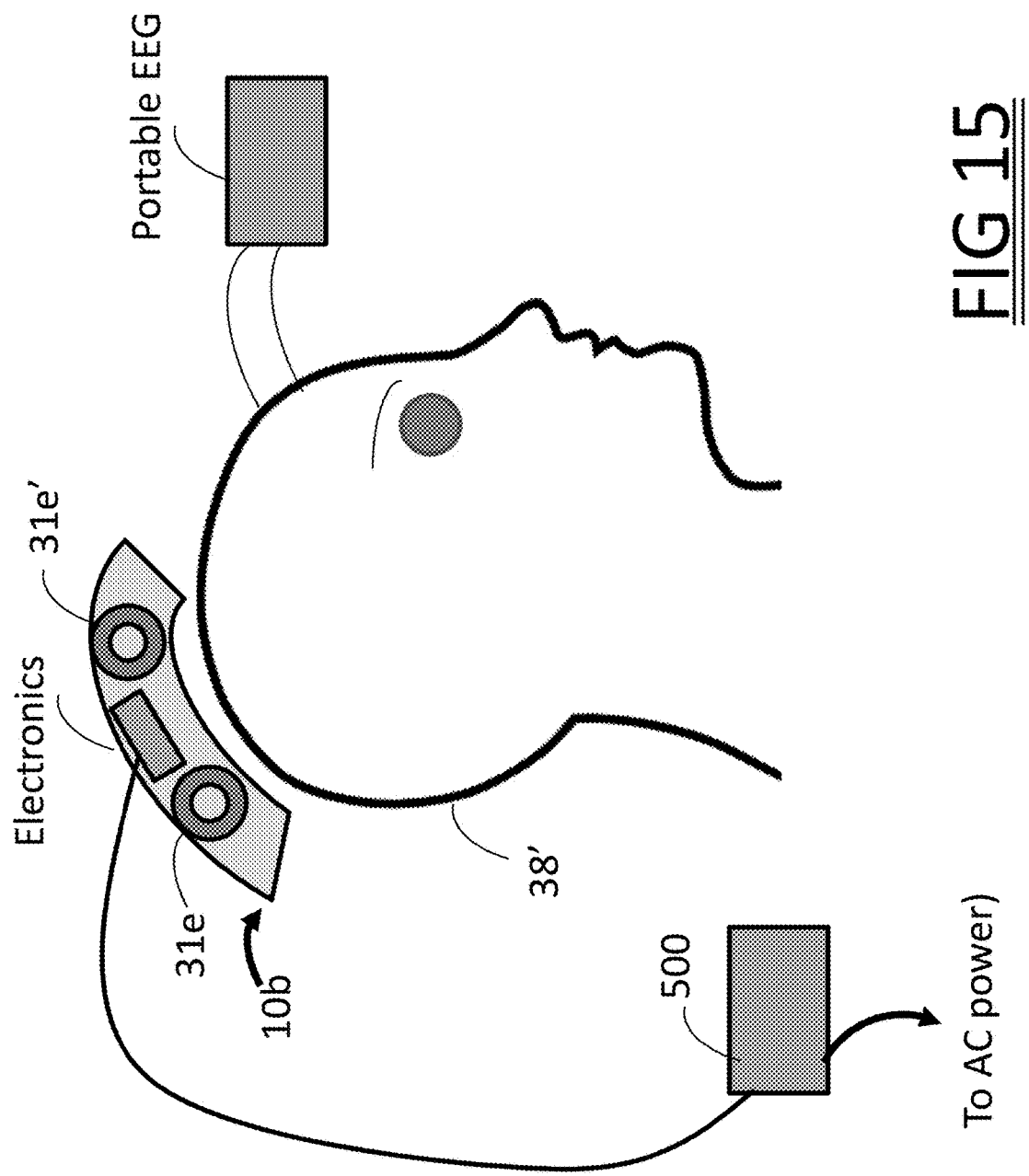

FIG. 15 Shows a device 10b for providing repetitive and/or responsive transcranial magnetic stimulation to a patient 38, who may be suffering a neurological disorder, such as been described in the '072 application. The device is a hand held or head-mounted structure containing circuitry to provide TMS from at least 2 magnetic-coil SEST-probes 31e and 31e'. The methods and systems of device 10a can be implemented in TMS device 10b, which can also communicate with a patient programmer 500. An AC power source for device 10b can be provided. The methods for using partial signals, roving protocol parameter values, and adjustment (e.g. matching) to endogenous activity are all applicable to stimulation provided by device 10b. The methods which involve matching the rate of stimulation to endogenous rhythms in the brain in order to increase the efficacy of treatment can be used in the rTMS treatment, where the pulses of the treatment are matched to internal oscillations. This type of treatment could be enabled, for example, using an EEG amplifier and an electrode attached to the surface of the patients head. The amplifier may be physically disconnected from the electrode during periods of pulsed magnetic stimulation so that currents are not induced in the electrode wire. The EEG measurements can be obtained in the periods between treatment pulses, which may occur in a regular, periodic manner or in response to evaluation of the EEG that is sensed. The use of partial signals can also be achieved by configuring the geometry of two or more stimulation coils appropriately with respect to the intended neural target.

When the rTMS treatment is used for treating disorders such as depression, the stimulation is can be primarily directed to the frontal areas of a patient's brain, and within the frontal areas the treatment may be primarily lateralized to either the left or right hemisphere, although both hemispheres can be treated. TMS applications can include induction or facilitation of anesthesia either with or without concurrent drug therapy, electrochemotherapy, therapies that affect the permeability of the blood brain barrier, applications of TMS to stroke recovery and other types of adaptation, the modulation of cellular and metabolic signals, and other therapeutic methods and applications.

Alternative Embodiments

It is recognized that the systems and methods of the present invention can be implemented using alternative neurostimulation devices and systems, without departing from the inventive principles disclosed herein. For example, rather than utilizing a sensing, stimulation, and control subsystem which provides therapy as guided by a treatment protocol, alternative devices may utilize functionally equivalent embodiments which rely upon treatment"rules", "templates", or"modules".

For example, U.S. Pat. No. 6,480,743 ('743 application) describes a device and methods which will be termed the NPACE system. The components of the device are: 1. detection subsystem and waveform analyzer; 2. stimulation subsystem and stimulation waveform generator; and, 3. a control interface. These are functionally equivalent to the 1. sensing subsystem and evaluation protocol; 2. stimulation subsystem and stimulation protocol; and 3 control subsystem and treatment program, respectively, which are utilized by the current invention. The NPACE system uses a method of detecting events which is similar to the event detection and evaluation of symptoms utilized in the current invention, and therapy templates of the NPACE system are similar to stimulation protocols utilized herein. It should be recognized that the systems and methods of the current invention can be implemented in the NPACE device in a similar fashion as described here, with different nomenclature, without departing from the spirit of the invention, and the steps of its methods, and strategies.

US20050240242 ('242 application) describes a device and method which will be termed the NBION system. The components of the device are: 1. sensor array and signal conditioning circuit; 2. control circuit; 3. output state circuit and stimulating electrode array, which are functionally equivalent to the 1. sensing subsystem; 2. control subsystem; and, 3. stimulation subsystem, of the current invention. The NBION system utilizes control laws and observers to provide neural modulation in the treatment of disease wherein a neural state is controlled to be maintained within a specified range. The neural state is similar to some of the types of sensed data of the current invention. The methods, algorithms, strategies, and principles of the current invention can therefore be easily implemented in the NBION system, and can provide methods for setting, evaluating, and adjusting the neurostimulation signals and treatment parameters of that system.

When using input signals, via control laws, event detection, or other strategy, to produce a stimulation signal which is used for neurostimulation, the output may not specifically defined has having constant properties since it is configured according to the characteristics of the sensed data. Nonetheless, control laws strategies can produce signals, partial signals, and vector fields similar or identical to those described herein, merely incidentally. It is understood that the advantageous characteristics of the signals and methods described herein can be incidentally produced without departing from the spirit of the inventions, and such incidental or non-determined creation of equivalent stimulation (for example, a signal with most of its energy below 20 Hz which is non-deterministically created by the output of a band-pass filter, a carrier signal which is approximately modulated according to the envelope of selected sensed activity, or two signals each directed to treat a different symptom of a disorder) is considered to be a subset of the disclosed methods. The disclosed methods cause roving to occur in a formalized and controlled manner so that the roving parameters provide increased therapeutic benefit to the patient.

Treatment.

Targets for therapy can be any part of an organism. Targets may be neural, vascular, in the brain spinal chord, heart, digestive system, or muscle or organ. Targets used in the treatment of epilepsy, migraine, psychiatric, neurodegenerative, memory, eating, pain, sleep, mood, anxiety, movement disorders, and tremors may include, but not be limited to the one or more regions of the hippocampus, brainstem, thalamus, cortex, and spinal chord, or at least one nerve structure comprises at least one of a trigeminal nerve, a branch of the trigeminal nerve, a trigeminal ganglion, an ophthalmic nerve, a branch of the ophthalmic nerve, a maxillary nerve, a branch of the maxillary nerve, a mandibular nerve, a branch of the mandibular nerve, a greater occipital nerve, a branch of the greater occipital nerve, a lesser occipital nerve, a branch of the lesser occipital nerve, a third occipital nerve, a branch of the third occipital nerve, a facial nerve, a branch of the facial nerve, a glossopharyngeal nerve, and a branch of the glossopharyngeal nerve.

The stimulation methods described herein can be used to stimulate tissue in order to modulate electrical, chemical or other types of activity, as well as cellular and developmental processes. The methods and systems for generating electrical fields can be applied to therapies and procedures related to growth and differentiation of cells (e.g., pre/post-implantation procedures related to stem or fetal cells), including neural differentiation which is induced by electrically stimulated gene expression (Mie et al, 2003). Further, the methods and systems can be used in conjunction with treatments such as chemotherapy in order to potentiate the response to or uptake of a chemotherapeutic agents or can be used independently as an anti-cancer therapy where electrical treatment of malignant tumors and neoplasms is provided by applying a stimulation approximately to affected tissue. Additionally the methods and systems can be used to modulate gene transfection, or alter the uptake of drugs by cells (e.g, electroporation, electropermeabilization, DNA electrotransfer) and can also be applied to modulate cellular growth and proliferation (Miklavcic et al., 1998; Faurie et al, 2004; Pucihar et al, 2002; Ciria et al, 2004; Cucullo et al., 2005). In these cases, great advantage may be obtained from using partial signals when stimulating focally in the 0.1 Hz to 20 Hz range, with respect to decreasing unwanted side-effects and assisting in patient tolerance to treatment. The stimulation can be used to alter cellular functioning, particularly protein synthesis, and alter synaptic transmission by modulating the production of neurotransmitters (Cucullo et al, 2005; Benabid & Wallace, 2005). The techniques can be used for wound healing, bone repair, and modulation of cellular activity and can also be used for prophylactic treatment. Further, the methods and systems can be used in dermatological treatment and cosmetic applications such as tissue reshaping and skin tightening, for example, by causing controlled patterns of damage, electroporation, thermal induction, wound healing, and collagen growth in selected tissue areas, such as skin, muscle, and fat. The systems and method can also be used to stimulate drugs or drug release, for example drugs stored within nano-particles which release these drugs when triggered by specific types of energy. The creation and utilization of partial signals described herein can be provided by implanted electrodes, or by optical transducers, or by external stimulation devices such as rTMS devices when used for applications such as electrochemotherapy, electroporation, and other relatively acute interventions. Stimulation, especially TMS, can be used to promote and modulate sedation and anesthesia.

The systems and methods described herein may be used in the treatment of psychiatric conditions, migraines, pain, tremor, OCD, anxiety, mania, and depression, traumatic brain injury or cerebovascular accidents, strokes, thrombosis or aneurysm, and can also be applied to stimulation of other areas of the body such as the cardiovascular system, digestive system, skin, muscle, spine, nerves related to pain, or other tissues or organs. Further the invention can be directed towards the provision of diagnostic applications such as neurological, neurosurgical, and neurophysiological testing, especially with respect to studies involving freezing (e.g., creating a functional lesion), activating, or functional mapping of selected regions, and testing of nerve conduction and nerve velocity in the diagnosis of any nerve degenerative disease. Testing and promotion of recovery can also be accomplished in post-TBI, and other disorders for which compensatory adaptation and retraining may promoted using stimulation. Stimulation of tissue can also be accompanied by, and time-locked to, sensory stimulation, can occur during tasks, and can occur during a period following drug administration.

The stimulation methods and systems of the current invention can be used in conjunction with priming techniques. For example, subthreshold or super-threshold stimulation can occur prior to, stimulation with any of the described techniques in order to facilitate, enhance, or diminish the response to the subsequent stimulation (e.g. Lyer et al, 2003). Likewise, post-stimulation modulation signals can be paired with stimulation signals in order to modulate, enhance, or diminish the response to the prior stimulation.

Terminology

The following material provides a general understanding of terms used in this specification, although these terms may have been further adjusted or modified or altered within the specification itself, or by reasonable and logical extrapolation, to achieve different specific embodiments of the invention.

As used herein the terms "stimulation system" or "stimulator" refers to a device having either distributed components or which are primarily contained within a device housing. Tissue modulation can include single (e.g. electrical), or multiple (e.g. optical and drug) therapy. The stimulator can be a generic implantable stimulator (e.g., Guidant, NeuroPace, Medtronic) adapted to achieve the inventive features. The stimulator can be a transcranial magnetic stimulator, or another modulation device, having components located partially or completely outside of the patient.

As used herein the term "module" refers to subroutines and hardware for realizing device operations. Modules may use resources of other modules (e.g. memory) to accomplish features of the invention. "Subsystems" refers to one or more modules which provide operations needed during therapy dictated by the treatment program.

As used herein the term "stimulation conduit" can include one or more electrical leads, each having at least one electrical contact. Stimulator conduits can also be any conduit which relays SEST-signals between SEST-probes and the device. When stimulation is drug-based then "fluid signals" can be transmitted by more catheters.

As used herein, the term "sensor" can refer to a device for measuring an electrical, chemical, optical, or other physical property of the patient. Sensors can be those described in US 20060149337, to John, entitled "Systems and methods for tissue stimulation in medical treatment".

As used herein, the term "treatment program" refers a set of subroutines to provide treatment using one or more "therapy/treatment protocols" and determines the parameters for the control, stimulation, sensing, and evaluation protocols, and determines, if, how, why, and when the protocols are altered. The terms "treatment" or "therapeutic benefit" can simply mean decreasing or deterring one or more unwanted symptoms of a disorder, or providing stimulation which is creates a therapeutic effect. Treatment can be related to treating a disorder, or can be related to inducing a medically/biologically related change in the patient, such as modulating anesthesia or sedation. The treatment can be directed towards preventing, deterring, normalizing and/or minimizing types of activity. The treatment program can provide therapy which minimizes energy or amount of stimulation needed to obtain therapeutic benefit increasing transmission of energy from stimulation sources to, and through, tissue. Treatment parameter values and protocols which produce advantageous effects are termed "successful".

As used herein "stimulation subsystem" provides stimulation according to the parameters of a stimulation protocol which determine where, if, when, and how to stimulate. A stimulus parameter value can define a spectral parameter, which relates to, for example, the amplitude, phase, and frequency of at least one component of the stimulation signal. A stimulus parameter can also be a pulse parameter, such as pulse frequency, amplitude, width or shape.

As used herein the terms "stimulation" refers to modulation of tissue which can be excitation, inhibition, or other type of desired modulation of target tissue. In the case of chemical-based therapy, stimulation signals may be include- "fluid signals," in the case of optical therapy these can include "light signals," and in the case of electrical therapy these can include "electrical signals."

As used herein, the terms "event", "detection of event" or "medical event" refer to the sensing and analysis of data which confirms that abnormal or unwanted activity, such as a seizure or other activity related to a symptom of a disorder was detected, predicted, or anticipated. Events may be abnormal states which have been detected or predicted.

As used herein, "symptom" generally refers to behavioral or electrophysiological signatures or specific components of a disorder. Symptoms can include: subjective experiences; abnormal activity, response to stimulation, or can be a neurochemical level, type of synchronization or coherence, metabolic or cellular activity, structural change, or network activity; abnormal data sensed from one or more sensors; a specific pattern or level of activity; or any other measure that is related to an abnormal trait or state related to the disorder.

As used herein, "roving" may refer to a function by which a parameter value is formally alternated over time. A parameter value can refer to voltage or current of a stimulation signal, and the value may be scaled or adjusted relative to impedance characteristics and/or electrode geometry, especially with regard to the generation of partial signals.

As used herein, "seizure" generally refers to behavioral or electrophysiological signature of an impending or existent seizure, and includes epileptiform activity.

As used herein, "amplitude" may refer to either voltage or current of a stimulation signal, and may be scaled or adjusted relative to impedance characteristics and/or electrode geometry.

As used herein the term "sensing subsystem" refers to a subsystem which provides sensing according to the parameters of a sensing protocol which determines where, when, if, and how to sense with one or more sensors. The sensing subsystem can provide communication with, and power and control signals to, sensors used in treatment.

As used herein the term "control subsystem" refers to a subsystem which provides control of the treatment and can implement a treatment program. The treatment program can select treatment protocols and parameter values from a database memory, and these parameters may be fixed, adjusted. The control system can communicate with an external patient programmer, or equivalent device through communication circuitry. The control system can implement sensing, stimulation, evaluation, calibration, and testing methods and algorithms as described herein. The control subsystem can also implement control laws to enact therapy.

As used herein the term "treatment criterion" refers to a criterion to which sensed data or test results are compared using the evaluation protocol. The results of this comparison can determine what type of stimulation takes place. For example, failure to meet a treatment criterion may cause stimulation to occur or may cause a change, or may cause a different stimulation protocol to be selected. Alternatively, success in meeting a treatment criterion may cause stimulation to be halted or may cause the same stimulation protocol to be selected again. It is obvious that the logic of treatment criterion can be inverted, and several criteria can be combined sequentially or in parallel in order to provide therapy without departing from the spirit of the invention illustrated and described in the embodiments of this description of the invention.

As used herein, "basal signal" or "basal stimulation" refers to the application of stimulation intended either to decrease the probability of an adverse event occurring, such as a seizure, or to modulate activity related to a disorder such as psychiatric illness or tremor. The basal signal is generally applied non-responsively, continuously, or periodically, although it can be adjusted or selected based upon the treatment program, time information, or sensed data.

As used herein, "base signal" normally refers to a signal which will be modified or used to determine two or more partial signals. The partial signals will combine to form a "vector sum field" in the tissue of the subject which approximates the base signal.

As used herein, "responsive" stimulation refers to the application of stimulation which occurs or is altered in response to evaluation of sensed data, such as the detection of a medical event.

The contents of all prior art examples cited in this specification and all scientific/technical references, are hereby incorporated by reference as if recited in full herein. In the claims of this application, when methods have steps which have been assigned letters, the steps may occur sequentially in the order indicated by the letters, or certain steps may occur approximately simultaneously, or in an interleaved fashion, with other steps. The stops of the methods can occur automatically using specialized algorithms, semi-automatically (with some manual adjustments), or primarily under the guidance of a physician. The headers for various sections such as "Background" or "Treatment" are intended to be descriptive only, and do not limit the scope of the material which is provided in these sections, in any way.

REFERENCES

Barr R C & Plonsey R (1992). Electrophysiological interaction through the interstitial space between adjacent unmyelinated parallel fibers. Biophys J 61, 1164-1175.

Basser P J & Roth B J (2000). New currents in electrical stimulation of excitable tissues. Annu Rev Biomed Eng 2, 377-397.

Bawin S M, Gavalas-Medici R J & Adey W R (1973). Effects of modulated very high frequency fields on specific brain rhythms in cats. Brain Res 58, 365-384.

Benabid A L, Wallace B, Mitrofanis J, Xia C, Piallat B, Fraix V, Batir A, Krack P, Pollak P & Berger F (2005). Therapeutic electrical stimulation of the central nervous system. C R Biol 328, 177-186.

Brasil-Neto J P, de Araujo D P, Teixeira W A, Araujo V P & Boechat-Barros R (2004). Experimental therapy of epilepsy with transcranial magnetic stimulation: lack of additional benefit with prolonged treatment. Arq Neuropsiquiatr 62, 21-25.

Bruet N, Windels F, Bertrand A, Feuerstein C, Poupard A & Savasta M (2001). High frequency stimulation of the subthalamic nucleus increases the extracellular contents of striatal dopamine in normal and partially dopaminergic denervated rats. J Neuropathol Exp Neurol 60, 15-24.

Bruet N, Windels F, Carcenac C, Feuerstein C, Bertrand A, Poupard A & Savasta M (2003). Neurochemical mechanisms induced by high frequency stimulation of the subthalamic nucleus: increase of extracellular striatal glutamate and GABA in normal and hemiparkinsonian rats. J Neuropathol Exp Neurol 62, 1228-1240.

Cemazar M, Miklavcic D, Mir L M, Belehradek J, Jr., Bonnay M, Fourcault D & Sersa G (2001). Electrochemotherapy of tumours resistant to cisplatin: a study in a murine to mou r model. Eur J Cancer 37, 1166-1172.

Ciria H C, Quevedo M S, Cabrales L B, Bruzon R P, Salas M F, Pena O G, Gonzalez T R, Lopez D S & Flores J M (2004). Antitumor effectiveness of different amounts of electrical charge in Ehrlich and fibrosarcoma Sa-37 tumors. BMC Cancer 4, 87.

Cucullo L, Dini G, Hallene K L, Fazio V, llkanich E V, lgboechi C, Kight K M, Agarwal M K, Garrity-Moses M & Janigro D (2005). Very low intensity alternating current decreases cell proliferation. Glia 51, 65-72.

D'Arcangelo G, Panuccio G, Tancredi V & Avoli M (2005). Repetitive low-frequency stimulation reduces epileptiform synchronization in limbic neuronal networks. Neurobiol Dis 19, 119-128.

Deurloo K E, Holsheimer J & Bergveld P (2001). The effect of subthreshold prepulses on the recruitment order in a nerve trunk analyzed in a simple and a realistic volume conductor model. Biol Cybern 85, 281-291.

Dinner D S (2002). Effect of sleep on epilepsy. J Clin Neurophysiol 19, 504-513.

Faurie C, Phez E, Golzio M, Vossen C, Lesbordes J C, Delteil C, Teissie J & Rols M P (2004). Effect of electric field vectoriality on electrically mediated gene delivery in mammalian cells. Biochim Biophys Acta 1665, 92-100.

Gerloff C, Cohen L G, Floeter M K, Chen R, Corwell B & Hallett M (1998). Inhibitory influence of the ipsilateral motor cortex on responses to stimulation of the human cortex and pyramidal tract. J Physiol 510 (Pt 1), 249-259.

Gerloff C, Corwell B, Chen R, Hallett M & Cohen L G (1997). Stimulation over the human supplementary motor area interferes with the organization of future elements in complex motor sequences. Brain 120 (Pt 9), 1587-1602.

Goodman J H, Berger R E & Tcheng T K (2005). Preemptive low-frequency stimulation decreases the incidence of amygdala-kindled seizures. Epilepsia 46, 1-7.

Graham-Jones S, Holt L, Gray J A & Fillenz M (1985). Low-frequency septal stimulation increases tyrosine hydroxylase activity in the hippocampus. Pharmacol Biochem Behav 23, 489-493.

Gray J A, Araujo-Silva M T & Quintao L (1972). Resistance to extinction after partial reinforcement training with blocking of the hippocampal theta rhythm by septal stimulation. Physiol Behav 8, 497-502.

Hoekema R, Venner K, Struijk J J & Holsheimer J (1998). Multigrid solution of the potential field in modeling electrical nerve stimulation. Comput Biomed Res 31, 348-362.

Holsheimer J, Nuttin B, King G W, Wesselink W A, Gybels J M & de Sutter P (1998). Clinical evaluation of paresthesia steering with a new system for spinal cord stimulation. Neurosurgery 42, 541-547; discussion 547-549.

Holsheimer J & Struijk J J (1991). How do geometric factors influence epidural spinal cord stimulation? A quantitative analysis by computer modeling. Stereotact Funct Neurosurg 56, 234-249.

Holsheimer J, Struijk J J & Rijkhoff N J (1991). Contact combinations in epidural spinal cord stimulation. A comparison by computer modeling. Stereotact Funct Neurosurg 56, 220-233.

Holsheimer J, Struijk J J & Tas N R (1995). Effects of electrode geometry and combination on nerve fibre selectivity in spinal cord stimulation. Med Biol Eng Comput 33, 676-682.

Holsheimer J & Wesselink W A (1997). Effect of anode-cathode configuration on paresthesia coverage in spinal cord stimulation. Neurosurgery 41, 654-659; discussion 659-660.

Holsheimer J & Wesselink W A (1997). Optimum electrode geometry for spinal cord stimulation: the narrow bipole and tripole. Med Biol Eng Comput 35, 493-497.

Holt L & Gray J A (1983). Proactive behavioral effects of theta-blocking septal stimulation in the rat. Behav Neural Biol 39, 7-21.

Holt L & Gray J A (1985). Proactive behavioral effects of theta-driving septal stimulation on conditioned suppression and punishment in the rat. Behav Neurosci 99, 60-74.

Irnich W (1999). Paradigm shift in lead design. Pacing Clin Electrophysiol 22, 1321-1332.

Iyer M B, Schleper N & Wassermann E M (2003). Priming stimulation enhances the depressant effect of low-frequency repetitive transcranial magnetic stimulation. J Neurosci 23, 10867-10872.

John E R, Leiman A L & Sachs E (1961). An exploration of the functional relationship between electroencephalographic potentials and differential inhibition. Ann N Y Acad Sci 92, 1160-1182.

Kasteleijn-Nolst Trenite D G & Vermeiren R (2005). The impact of subclinical epileptiform discharges on complex tasks and cognition: relevance for aircrew and air traffic controllers. Epilepsy Behav 6, 31-34.

Katayama Y, Yamamoto T, Kobayashi K, Oshima H & Fukaya C (2003). Deep brain and motor cortex stimulation for post-stroke movement disorders and post-stroke pain. Acta Neurochir Suppl 87, 121-123.

Kim Y, Zieber H G & Wang F E (1990). Uniformity of current density under stimulating electrodes. Crit Rev Biomed Eng 17, 585-619.

Kinoshita M, Ikeda A, Begum T, Yamamoto J, Hitomi T & Shibasaki H (2005). Low-frequency repetitive transcranial magnetic stimulation for seizure suppression in patients with extratemporal lobe epilepsy-A pilot study. Seizure 14, 387-392.

Kinoshita M, Ikeda A, Matsumoto R, Begum T, Usui K, Yamamoto J, Matsuhashi M, Takayama M, Mikuni N, Takahashi J, Miyamoto S & Shibasaki H (2004). Electric stimulation on human cortex suppresses fast cortical activity and epileptic spikes. Epilepsia 45, 787-791.

Kossoff E H, Ritzl E K, Politsky J M, Murro A M, Smith J R, Duckrow R B, Spencer D D & Bergey G K (2004). Effect of an external responsive neurostimulator on seizures and electrographic discharges during subdural electrode monitoring. Epilepsia 45, 1560-1567.

Kovner R & Stamm J S (1972). Disruption of short-term visual memory by electrical stimulation of inferotemporal cortex in the monkey. J Comp Physiol Psychol 81, 163-172.

Krnjevic K, Morris M E & Reiffenstein R J (1982). Stimulation-evoked changes in extracellular K+ and Ca2+ in pyramidal layers of the rat's hippocampus. Can j Physiol Pharmacol 60, 1643-1657.

Kuncel A M & Grill W M (2004). Selection of stimulus parameters for deep brain stimulation. Clin Neurophysiol 115, 2431-2441.

Lertmanorat Z & Durand D M (2004). Extracellular voltage profile for reversing the recruitment order of peripheral nerve stimulation: a simulation study. J Neural Eng 1, 202-211.

Lertmanorat Z & Durand D M (2004). A novel electrode array for diameter-dependent control of axonal excitability: a simulation study. IEEE Trans Biomed Eng 51, 1242-1250.

Manola L, Roelofsen B H, Holsheimer J, Marani E & Geelen J (2005). Modelling motor cortex stimulation for chronic pain control: electrical potential field, activating functions and responses of simple nerve fibre models. Med Biol Eng Comput 43, 335-343.

Matsuda Y, Yano M, Kitayama M, Kogure S & Yamauchi T (2003). Epileptogenesis induced by alternate-site kindling in bilateral hippocampi. Epilepsia 44, 292-298.

Mcintyre C C & Grill W M (1999). Excitation of central nervous system neurons by nonuniform electric fields. Biophys J 76, 878-888.

Mcintyre C C & Grill W M (2000). Selective microstimulation of central nervous system neurons. Ann Biomed Eng 28, 219-233.

Mcintyre C C & Grill W M (2001). Finite element analysis of the current-density and electric field generated by metal microelectrodes. Ann Biomed Eng 29, 227-235.

Mcintyre C C & Grill W M (2002). Extracellular stimulation of central neurons: influence of stimulus waveform and frequency on neuronal output. J Neurophysiol 88, 1592-1604.

Mcintyre C C, Grill W M, Sherman D L & Thakor N V (2004). Cellular effects of deep brain stimulation: model-based analysis of activation and inhibition. J Neurophysiol 91, 1457-1469.

Mcintyre C C, Mori S, Sherman D L, Thakor N V & Vitek J L (2004). Electric field and stimulating influence generated by deep brain stimulation of the subthalamic nucleus. Clin Neurophysiol 115, 589-595.

Menkes D L & Gruenthal M (2000). Slow-frequency repetitive transcranial magnetic stimulation in a patient with focal cortical dysplasia. Epilepsia 41, 240-242.

Mie M, Endoh T, Yanagida Y, Kobatake E & Aizawa M (2003). Induction of neural differentiation by electrically stimulated gene expression of NeuroD2. J Biotechnol 100, 231-238.

Miklavcic D, Berays K, Semrov D, Cemazar M, Demsar F & Sersa G (1998). The importance of electric field distribution for effective in vivo electroporation of tissues. Biophys J 74, 2152-2158.

Miklavcic D, Pucihar G, Paviovec M, Ribaric S, Mali M, Macek-Lebar A, Petkovsek M, Nastran J, Kranjc S, Cemazar M & Sersa G (2005). The effect of high frequency electric pulses on muscle contractions and antitumor efficiency in vivo for a potential use in clinical electrochemotherapy. Bioelectrochemistry 65, 121-128.

Misawa S, Kuwabara S, Shibuya K, Mamada K & Hattori T (2005). Low-frequency transcranial magnetic stimulation for epilepsia partialis continua due to cortical dysplasia. J Neurol Sci 234, 37-39.

Miyoshi S, Shimizu S, Matsushima J & Ifukube T (1999). Proposal of a new method for narrowing and moving the stimulated region of cochlear implants: animal experiment and numerical analysis. IEEE Trans Biomed Eng 46, 451-460.

Moro E, Esselink R J, Xie J, Hommel M, Benabid A L & Pollak P (2002). The impact on Parkinson's disease of electrical parameter settings in STN stimulation. Neurology 59, 706-713.

Mutani R & Fariello R (1969). Effect of low frequency caudate stimulation on the EEG of epileptic neocortex. Brain Res 14, 749-753.

Nakagawa M & Durand D (1991). Suppression of spontaneous epileptiform activity with applied currents. Brain Res 567, 241-247.

Nakamura S (1975). Two types of inhibitory effects upon brain stem reticular neurons by low frequency stimulation of raphe nucleus in the rat. Brain Res 93, 140-144.

Plonsey R & Barr R C (1995). Electric field stimulation of excitable tissue. IEEE Trans Biomed Eng 42, 329-336.

Plonsey R & Barr R C (1998). Electric field stimulation of excitable tissue. IEEE Eng Med Biol Mag 17, 130-137.

Puc M, Corovic S, Flisar K, Petkovsek M, Nastran J & Miklavcic D (2004). Techniques of signal generation required for electropermeabilization. Survey of electropermeabilization devices. Bioelectrochemistry 64, 113-124.

239 Pucihar G, Mir L M & Miklavcic D (2002). The effect of pulse repetition frequency on the uptake into electropermeabilized cells in vitro with possible applications in electrochemotherapy. Bioelectrochemistry 57, 167-172.

Pumir A, Plaza F & Krinsky V I (1994). Effect of an externally applied electric field on excitation propagation in the cardiac muscle. Chaos 4, 547-555.

Rattay F & Resatz S (2004). Effective electrode configuration for selective stimulation with inner eye prostheses. IEEE Trans Biomed Eng 51, 1659-1664.

Rossi S, Ulivelli M, Bartalini S, Galli R, Passero S, Battistini N & Vatti G (2004). Reduction of cortical myoclonus-related epileptic activity following slow-frequency rTMS. Neuroreport 15, 293-296.

Santos-Anderson R M & Routtenberg A (1976). Stimulation of rat medial or sulcal prefrontal cortex during passive avoidance learning selectively influences retention performance. Brain Res 103, 243-259.

Satkauskas S, Andre F, Bureau M F, Scherman D, Miklavcic D & Mir L M (2005). Electrophoretic Component of Electric Pulses Determines the Efficacy of In Vivo DNA Electrotransfer. Hum Gene Ther.

Sepulveda N G, Walker C F & Heath R G (1983). Finite element analysis of current pathways with implanted electrodes. J Biomed Eng 5, 41-48.

Skelton R W, Miller J J & Phillips A G (1983). Low-frequency stimulation of the perforant path produces long-term potentiation in the dentate gyrus of unanesthetized rats. Can J Physiol Pharmacol 61, 1156-1161.

Struijk J J & Holsheimer J (1996). Transverse tripolar spinal cord stimulation: theoretical performance of a dual channel system. Med Biol Eng Comput 34, 273-279.

Struijk J J, Holsheimer J, Spincemaille G H, Gielen F L & Hoekema R (1998). Theoretical performance and clinical evaluation of transverse tripolar spinal cord stimulation. IEEE Trans Rehabil Eng 6, 277-285.

Susil R C, Sobie E A & Tung L (1999). Separation between virtual sources modifies the response of cardiac tissue to field stimulation. J Cardiovasc Electrophysiol 10, 715-727.

Tai C, de Groat W C, Roppolo J R. Simulation of nerve block by high-frequency sinusoidal electrical current based on the Hodgkin-Huxley model. IEEE Trans Neural Syst Rehabil Eng. 2005 September; 13(3):415-22.

Tergau F, Naumann U, Paulus W & Steinhoff B J (1999). Low-frequency repetitive transcranial magnetic stimulation improves intractable epilepsy. Lancet 353, 2209.

Ueno S T, T; Harada. k (1988). Localized stimulation of neural tissues in the brain by means of paried configuration of time-varying magnetic fields. Journal of Applied Phys. 64, 5862-5864.

Velisek L, Dreier J P, Stanton P K, Heinemann U & Moshe S L (1994). Lowering of extracellular pH suppresses low-Mg(2+)-induces seizures in combined entorhinal cortex-hippocampal slices. Exp Brain Res 101, 44-52.

Velisek L, Veliskova J & Stanton P K (2002). Low-frequency stimulation of the kindling focus delays basolateral amygdala kindling in immature rats. Neurosci Lett 326, 61-63.

Weiss S R, Li X L, Rosen J B, Li H, Heynen T & Post R M (1995). Quenching: inhibition of development and expression of amygdala kindled seizures with low frequency stimulation. Neuroreport 6, 2171-2176.

Wieraszko A (2004). Amplification of evoked potentials recorded from mouse hippocampal slices by very low repetition rate pulsed magnetic fields. Bioelectromagnetics 25, 537-544.

Windels F, Bruet N, Poupard A, Feuerstein C, Bertrand A & Savasta M (2003). Influence of the frequency parameter on extracellular glutamate and gamma-aminobutyric acid in substantia nigra and globus pallidus during electrical stimulation of subthalamic nucleus in rats. J Neurosci Res 72, 259-267.

Yamamoto T, Katayama Y, Fukaya C, Oshima H, Kasai M & Kobayashi K (2001). New method of deep brain stimulation therapy with two electrodes implanted in parallel and side by side. J Neurosurg 95, 1075-1078.

What is claimed is:

1. A system for transcranial magnetic stimulation, the system comprising:
   at least a first electromagnetic stimulating coil configured for providing a first partial signal field;
   at least a second electromagnetic stimulating coil configured for providing a second partial signal field, wherein the first coil and second coil are further configured to be sufficiently close and oriented to cause at least the partial summation of the first and second partial signal fields in order to approximately create a vector signal in at least a portion of a neural target of a deep brain region; and,
   a control subsystem designed to control stimulation circuitry that is designed for creating and providing a first partial stimulation signal at the first stimulating coil and second partial stimulating signal at the second coil, wherein at least one of the first and second stimulating signals has a selected frequency or temporal characteristic that is selected to match a characteristic of brain activity of a patient and the signals are defined to produce a vector stimulation signal in approximately said neural target of a deep brain region, said vector stimulation signal being designed to provide therapy to the patient.

2. The system for transcranial magnetic stimulation of claim 1, wherein the first and second stimulating signals each have a unique frequency or temporal characteristic selected to be different for the first and second signal.

3. The system for transcranial magnetic stimulation of claim 1, wherein the vector signal field is designed so that it matches a characteristic of brain activity of the patient, wherein that activity is selected to be one of the peak alpha activity of the patient and the peak theta activity of the patient.

4. The system for transcranial magnetic stimulation of claim 1, further including a database for allowing the control subsystem to store, retrieve, and select treatment protocols and parameter values.

5. The system for transcranial magnetic stimulation of claim 1, further including a sensor, sensing subsystem, and evaluation subsystem for sensing and evaluating sensed data of the patient.

6. The system for transcranial magnetic stimulation of claim 5, wherein the evaluation subsystem operates to evaluate said sensed data using at least one treatment criterion in order to assess the effects of the transcranial magnetic stimulation.

7. A method for providing transcranial magnetic stimulation, the method comprising:
   operating at least a first electromagnetic stimulating coil configured for providing a first partial signal;
   operating at least a second electromagnetic stimulating coil configured for providing a second partial signal field, wherein the first coil and second coil are further configured to be sufficiently close and oriented to cause at least the partial summation of the first and second partial signal fields in order to approximately create a vector signal in at least a portion of a neural target of a deep brain region; and,
   operating a control subsystem designed to control stimulation circuitry that is designed for creating and providing a first partial stimulation signal at the first stimulating coil and second partial stimulating signal at the second coil, wherein least one of the first and second stimulating signals has a selected frequency or temporal characteristic that is selected to match a characteristic of brain activity of a patient, and the signals are defined to produce a vector stimulation signal in approximately said neural target of a deep brain region, said vector stimulation signal being designed to provide therapy to the patient.

8. The method for providing transcranial magnetic stimulation of claim 7, wherein the first and second stimulating signals each have a unique frequency or temporal characteristic selected to be different for the first and second signal.

9. The method for providing transcranial magnetic stimulation of claim 7, wherein the first partial signal field is designed so that it does not produce stimulation of neural tissue located in a non-target region in the same manner as that which occurs in the neural target.

10. The method for providing transcranial magnetic stimulation of claim 7, wherein the vector signal field is designed so that it matches a characteristic of brain activity sensed from the patient wherein that activity is selected to be one of the peak alpha activity of the patient and the peak theta activity of the patient.

11. The method for providing transcranial magnetic stimulation of claim 7, further including operating a database for allowing the control subsystem to store, retrieve, and select treatment protocols and parameter values.

12. The method for providing transcranial magnetic stimulation of claim 7, further including operating a sensor, sensing subsystem, and evaluation subsystem for sensing and evaluating sensed data of the patient.

13. The method for providing transcranial stimulation of claim 12, wherein the evaluation subsystem is operated to evaluate said sensed data using at least one treatment criterion in order to assess the effects of the transcranial magnetic stimulation.

14. The method for providing transcranial stimulation of claim 12, wherein the evaluation subsystem is operated to evaluate said sensed data to detect a peak frequency in an alpha or theta band of a patient's EEG and adjust at least one characteristics of the transcranial magnetic stimulation.

15. The method for providing transcranial stimulation of claim 7 wherein the first and second partial signal are selected to provide a vector stimulation signal having a windowed pulse train forming a repetitive bursting pattern.

16. The method of claim 7 wherein the therapy is related to the treatment of at least one psychiatric condition.

17. The method of claim 7 wherein the therapy is related to the treatment of depression.

18. The method of claim 7 wherein the therapy is related to the treatment of migraine.

19. The method of claim 7 wherein at least one partial signal field is adjusted based upon the evaluation of sensed data including sensed data from the heart.

20. A method for providing transcranial magnetic stimulation, the method comprising:

operating at least a first electromagnetic stimulating coil configured for providing a first partial signal field;

operating at least a second electromagnetic stimulating coil configured for providing a second partial signal field, wherein the first coil and second coil are further configured to be sufficiently close and oriented to cause at least the partial summation of the first and second partial signal fields in order to approximately create a vector signal in at least a portion of a neural target of a deep brain region; and, operating a control subsystem designed to control stimulation circuitry that is designed for creating and providing a first partial stimulation signal at the first stimulating coil and second partial stimulating signal at the second coil, wherein least one of the first and second stimulating signals has a selected frequency or temporal characteristic that is selected to not-match a characteristic of brain activity of a patient, and the signals are defined to produce a vector stimulation signal in approximately said neural target of a deep brain region, said vector stimulation signal being designed to provide therapy to the patient.

* * * * *